(12) United States Patent
Donaldson

(10) Patent No.: US 10,046,147 B2
(45) Date of Patent: Aug. 14, 2018

(54) PERCUTANEOUS ACCESS PATHWAY SYSTEM AND METHOD

(71) Applicant: Critical Innovations, LLC, Venice, CA (US)

(72) Inventor: Ross I. Donaldson, Venice, CA (US)

(73) Assignee: CRITICAL INNOVATIONS, LLC, Venice, CA (US)

( * ) Notice: Subject to any disclaimer, the term of this patent is extended or adjusted under 35 U.S.C. 154(b) by 541 days.

(21) Appl. No.: 14/581,339

(22) Filed: Dec. 23, 2014

(65) Prior Publication Data

US 2015/0182733 A1 Jul. 2, 2015

Related U.S. Application Data

(60) Provisional application No. 61/920,963, filed on Dec. 26, 2013.

(51) Int. Cl.
| | | |
|---|---|---|
| *A61M 1/04* | (2006.01) | |
| *A61M 27/00* | (2006.01) | |
| *A61B 17/34* | (2006.01) | |
| *A61M 25/06* | (2006.01) | |

(Continued)

(52) U.S. Cl.
CPC ............ *A61M 27/00* (2013.01); *A61B 17/34* (2013.01); *A61B 17/3415* (2013.01); *A61B 17/3496* (2013.01); *A61M 1/04* (2013.01); *A61M 25/0606* (2013.01); *A61B 90/40* (2016.02);

(Continued)

(58) Field of Classification Search
CPC . A61B 17/34; A61B 17/3415; A61B 17/3496; A61B 2017/00809; A61B 2017/3409; A61B 90/40; A61M 2210/101; A61M 1/04; F16L 37/24; F16L 37/248
See application file for complete search history.

(56) References Cited

U.S. PATENT DOCUMENTS

| | | | |
|---|---|---|---|
| 3,777,757 A | 12/1973 | Gray et al. | |
| 3,789,852 A | 2/1974 | Kim et al. | |
| 3,894,540 A | 7/1975 | Bonner, Jr. | |

(Continued)

FOREIGN PATENT DOCUMENTS

| | | |
|---|---|---|
| CN | 1756513 B | 4/2006 |
| EP | 2 168 558 A1 | 3/2010 |

(Continued)

OTHER PUBLICATIONS

Search Report dated Nov. 8, 2013 for EP Application No. 13179479.4 filed Aug. 6, 2013, 5 pages.

(Continued)

*Primary Examiner* — Tatyana Zalukaeva
*Assistant Examiner* — Kai Weng
(74) *Attorney, Agent, or Firm* — Patterson Thuente Pedersen, P.A.

(57) ABSTRACT

An improved method and device are provided for forming and/or maintaining a percutaneous access pathway. The device generally comprises at least one of three type of components: access pathway, insertion device, and attachment device. In one embodiment, the device is used to form and/or maintain a percutaneous access pathway into the pleural cavity (i.e. tube thoracostomy). The provided assembly substantially reduces the possibility of iatrogenic infection while accessing and/or re-accessing a body space.

15 Claims, 16 Drawing Sheets

(51) Int. Cl.
    *A61B 17/00*     (2006.01)
    *A61B 90/40*     (2016.01)

(52) U.S. Cl.
    CPC ............... *A61B 2017/00809* (2013.01); *A61B 2017/3409* (2013.01); *A61M 2210/101* (2013.01)

(56) References Cited

U.S. PATENT DOCUMENTS

| | | |
|---|---|---|
| 4,153,058 A | 5/1979 | Nehme |
| 4,164,938 A | 8/1979 | Patton |
| 4,221,215 A | 9/1980 | Mandelbaum |
| 4,392,853 A | 7/1983 | Muto |
| 4,617,011 A | 10/1986 | Bloxom, Jr. |
| 4,664,660 A | 5/1987 | Goldberg et al. |
| 4,767,409 A | 8/1988 | Brooks |
| 4,767,411 A | 8/1988 | Edmunds |
| 4,944,724 A | 7/1990 | Goldberg et al. |
| 5,098,388 A | 3/1992 | Kulkashi et al. |
| 5,207,647 A | 5/1993 | Phelps |
| 5,215,522 A | 6/1993 | Page et al. |
| 5,215,531 A | 6/1993 | Maxson et al. |
| 5,242,398 A | 9/1993 | Knoll et al. |
| 5,256,148 A | 10/1993 | Smith et al. |
| 5,263,939 A | 11/1993 | Wortrich |
| 5,284,474 A * | 2/1994 | Adair ............... A61B 17/3496 604/164.12 |
| 5,300,046 A | 4/1994 | Scarfone et al. |
| 5,334,159 A | 8/1994 | Turkel |
| 5,336,193 A | 8/1994 | Rom et al. |
| 5,376,082 A | 12/1994 | Phelps |
| 5,421,821 A | 6/1995 | Janicki |
| 5,429,608 A | 7/1995 | Rom et al. |
| 5,478,333 A | 12/1995 | Asherman, Jr. |
| 5,514,111 A | 5/1996 | Phelps |
| 5,520,650 A | 5/1996 | Zadini et al. |
| 5,545,179 A | 8/1996 | Williamson, IV |
| 5,660,883 A | 8/1997 | Omura |
| 5,662,616 A | 9/1997 | Bousquet |
| 5,685,852 A | 11/1997 | Turkel et al. |
| 5,725,506 A | 3/1998 | Freeman et al. |
| 5,807,341 A | 9/1998 | Heim |
| 5,827,221 A | 10/1998 | Phelps |
| 5,897,531 A | 4/1999 | Amirana |
| 5,902,273 A | 5/1999 | Yang et al. |
| 5,997,486 A | 12/1999 | Burek et al. |
| 6,019,735 A | 2/2000 | Kensey et al. |
| 6,221,048 B1 | 4/2001 | Phelps |
| 6,402,770 B1 | 6/2002 | Jessen |
| 6,447,483 B1 | 9/2002 | Steube et al. |
| 6,605,063 B2 | 8/2003 | Bousquet |
| 6,638,253 B2 | 10/2003 | Breznock |
| 6,770,070 B1 | 8/2004 | Balbierz |
| 6,905,484 B2 | 6/2005 | Buckman et al. |
| 7,135,010 B2 | 11/2006 | Buckman et al. |
| 7,229,433 B2 | 6/2007 | Mullen |
| 7,244,245 B2 | 7/2007 | Purow et al. |
| 7,429,687 B2 | 9/2008 | Kauth et al. |
| 7,615,674 B2 | 11/2009 | Asherman |
| 7,789,873 B2 | 9/2010 | Kubalak et al. |
| 7,811,293 B2 | 10/2010 | Simpson et al. |
| 7,824,366 B2 | 11/2010 | Tanaka |
| 7,842,058 B2 | 11/2010 | Simpson et al. |
| 8,057,443 B2 | 11/2011 | McNeil |
| 8,062,315 B2 | 11/2011 | Aster et al. |
| 8,128,648 B2 | 3/2012 | Hassidov et al. |
| 8,430,094 B2 | 4/2013 | Tanaka et al. |
| 8,518,053 B2 | 8/2013 | Tanaka et al. |
| 9,616,203 B2 | 4/2017 | Donaldson |
| 2003/0073960 A1 | 4/2003 | Adams et al. |
| 2003/0233073 A1 | 12/2003 | Purow et al. |
| 2004/0078026 A1 | 4/2004 | Wagner |
| 2004/0133226 A1 | 7/2004 | Buckman et al. |
| 2006/0025723 A1 | 2/2006 | Ballarini |
| 2007/0021768 A1 | 1/2007 | Nance et al. |
| 2007/0038180 A1 | 2/2007 | Sinha et al. |
| 2008/0103451 A1 | 5/2008 | Schaefer, Jr. et al. |
| 2008/0125750 A1 | 5/2008 | Gaissert |
| 2008/0312638 A1 | 12/2008 | McNeil |
| 2009/0005800 A1 | 1/2009 | Franer et al. |
| 2009/0205646 A1 | 8/2009 | Tanaka et al. |
| 2009/0205651 A1 | 8/2009 | Tanaka et al. |
| 2009/0318898 A1 | 12/2009 | Dein |
| 2010/0170507 A1 | 7/2010 | Tanaka et al. |
| 2010/0204707 A1 | 8/2010 | Tanaka et al. |
| 2011/0054340 A1 | 3/2011 | Russ et al. |
| 2011/0152874 A1 | 6/2011 | Lyons |
| 2012/0051967 A1 | 3/2012 | Murphy et al. |
| 2012/0191044 A1 | 7/2012 | Koike |
| 2012/0209166 A1 | 8/2012 | Power et al. |
| 2013/0131645 A1 | 5/2013 | Tekulve |
| 2014/0046303 A1 | 2/2014 | Donaldson |
| 2017/0182229 A1 | 6/2017 | Donaldson |

FOREIGN PATENT DOCUMENTS

| | | |
|---|---|---|
| GB | 2140301 A | 11/1984 |
| WO | WO 2008/029109 A1 | 3/2008 |

OTHER PUBLICATIONS

File history for U.S. Appl. No. 13/961,422, filed Aug. 7, 2013. Inventor: Ross I. Donaldson.
Robert Mabry et al., "Prehospital advances in the management of severe penetrating trauma", Crit Care Med 2008 vol. 36, No. 7 (Suppl.) 9 pages.
S. Leigh-Smith et al., "Tension pneumothorax—time for a re-think?" *Emerg Med J* 2005 vol. 22, pp. 8-16.
William Benedict Maxwell et al., "The Hanging Drop to Locate the Pleural Space: A Safer Method for Decompression of Suspected Tension Pneumothorax?", *The Journal of Trauma, Injury, Infection, and Critical Care*, vol. 69, No. 4, Oct. 2010, 2 pages.
Erik K. Bassett et al., "Design of a mechanical clutch-based needle-insertion device", *PNAS Early Edition*, Aug. 25, 2008, 6 pages.
EP Application No. 13179479.4, Examination Report dated Feb. 7, 2017, 3 pages.
EP Application No. EP13179479.4, Examination Report dated Oct. 5, 2017, 3 pages.
Application and File History for U.S. Appl. No. 15/448,680, filed Mar. 3, 2017. Inventor: Donaldson.
Search Report for European Patent Application No. 14200292.2 dated May 22, 2015, 8 pages.
Communication pursuant to Article 94(3) EPC from European Application No. 14200292.2, dated Feb. 26, 2018 (6 pages).

* cited by examiner

PERCUTANEOUS ACCESS PATHWAY SYSTEM AND METHOD

RELATED APPLICATIONS

The present application claims the benefit of U.S. Provisional Application No. 61/920,963 filed Dec. 26, 2013, which is incorporated herein in its entirety by reference. U.S. patent application Ser. No. 13/961,422, filed Aug. 7, 2013 and entitled Method and Device for Simultaneously Documenting and Treating Tension Pneumothorax and/or Hemothorax, having the same inventor as the present application, is also hereby incorporated by reference herein in its entirety.

FIELD OF THE INVENTION

The present disclosure relates generally to the field of medical devices, and more particularly, to devices and methods for forming and/or maintaining a percutaneous access pathway. In one application, the present invention relates to methods and devices for draining air and/or fluids from the body of a patient.

BACKGROUND OF THE INVENTION

A wide variety of diagnostic and/or therapeutic procedures involves the introduction of a device through a natural or artificially created percutaneous access pathway in a body of a patient. One of the general objectives of access systems developed for this purpose is to minimize the chances of iatrogenic injury to the patient, including laceration of vital structures or the introduction of infectious organisms from the skin or external environment into the body.

Tube thoracostomy (i.e. the percutaneous placement of a chest tube into the pleural space) is an example of one type of interventional procedure that requires an artificially created pathway. There are several possible reasons for needing to place a chest tube into the pleural space (the space between the visceral pleura covering a lung and the parietal pleura covering the inside of the chest wall). These reasons may be medical or traumatic in nature, and include the drainage of a wide range of fluids, such as blood (hemothorax), air (pneumothorax), pleural effusion, serous fluid (hydrothorax), chyle (chylothorax), and pus (pyothorax).

There are several methods currently employed to place a chest tube into the body. The chest tube may be inserted by pushing it through the chest wall over a sharp trocar, although this risks lacerating the underlying organs with the sharp trocar. Tube thoracostomy is typically performed via an open surgical approach, which involves cutting the skin with a scalpel and then dilating the underlying tissues with a forceps or other blunt instrument before inserting one or more chest tubes. This multistep process still risks lacerating the neurovascular bundle underneath the rib, but has less chance of damaging deeper organs. Alternatively, the Seldinger technique is another option, wherein a needle is initially advanced, then a guide wire inserted through the needle, the needle is removed, dilator(s) are positioned over the wire, and finally the chest tube is placed. This has less chance of damaging vital structures, but is lengthy in practice.

All current methods share some drawbacks including the aforementioned risks of damaging underlying structures, as well as the need to perform tube thoracostomy under a relatively large sterile field due to chest tube length. This makes it difficult to maintain sterility outside of the operating room, for example in the emergency department, in the out-of-hospital arena, or on the battlefield. Additionally, the portion of the chest tube outside the body immediately becomes unsterile after finishing the procedure. Thus, the chest tube should not be moved further into the patient after initial placement if it was inserted too shallowly or becomes dislodged. Similarly, if the tube becomes irreversibly clogged, a sterile field needs to be reestablished in order to replace the chest tube.

Roberts and Hedges' *Clinical Procedures in Emergency Medicine*, 6th ed. "Chapter 10—Tube Thoracostomy." 2013, Saunders, contains additional information regarding tube thoracostomy.

The literature discloses various additional known methods and devices for forming and/or maintaining a percutaneous access pathway, many of which are improvements specifically regarding tube thoracostomy.

For example, U.S. Publication No. 2007/0038180 to Sinha et al. describes a chest tube insertion gun that pushes the chest tube through the chest wall using a sharp trocar. This is a mechanical version of the trocar method and it still has the noted drawback of potential injury to underlying organs from the sharp trocar.

U.S. Publication No. 2006/0025723 to Ballarini and U.S. Pat. No. 5,897,531 to Amirana describe devices for securing a chest tube to the external skin of a patient. Although this helps hold the tube after placement, it does not establish a percutaneous entrance. U.S. Publication No. 2008/0103451 to Schaefer and U.S. Pat. No. 4,221,215 to Mandelbaum, U.S. Pat. No. 5,215,531 to Maxson et al., and U.S. Pat. No. 5,263,939 to Wortrich are other similar examples of external anchoring mechanisms for percutaneous tubes. Similarly, U.S. Pat. No. 6,638,253 to Breznock describes a chest tube with an internal check valve, distal holes that open using a central rod, and a balloon holding the device inside the patient. Although this anchors the tube to the patient from the inside, it does not reduce the chance of iatrogenic injury or infection.

Several prior works describe the placement of percutaneous access pathway ports into the body, which allow entrance into inner cavities. Chinese Patent No. 1,756,513B and U.S. Pat. Nos. 7,811,293 and 7,842,058 to Simpson et al. describe a cutting gun that inserts a port for chest tube placement. After port placement, a chest tube can be inserted into the body thought the port opening. However, this still has the limitations of possible iatrogenic laceration of underlying vital structures with the sharp moving blades, as well as difficulty maintaining a sterile field outside of the operating room.

Other transcutaneous ports include mechanisms for reduced infection risk and pain. For example, U.S. Pat. No. 3,777,757 to Gray et al. describes an inflatable chest tube port to increase patient comfort. Others include U.S. Pat. No. 3,789,852 to Kim et al.; U.S. Pat. No. 5,545,179 to Williamson, I V; and U.S. Pat. No. 4,767,411 to Edmunds and U.S. Publication No. 2004/0078026 to Wagner. Further, U.S. Pat. Nos. 8,518,053; 8,430,094; and 7,824,366 and U.S. Publication Nos. 2009/0205646; 2010/0170507; and 2009/0205651 to Tanaka, et al., as well as U.S. Pat. No. 8,062,315 to Aster et al. all describe transcutaneous ports placed to specifically establish a pneumostoma (a transcutaneous hole terminating inside the lung tissue itself, as opposed to the pleural space around the lung in tube thoracostomy). However, these do not significantly mitigate the limitations of transcutaneous port insertion.

Prior works describe some improvements in transcutaneous access via the use of expanding catheters or other dilatational devices. For example, U.S. Publication No. 2013/0131645 to Tekulve describes a chest tube that has an internal diameter that inflates and deflates to remove clogged blood. However, this is only an internal mechanism and does not significantly change the external diameter of the chest tube. U.S. Publication No. 2007/0021768 to Nance et al. describes an expandable tube for nephrostomy procedures, however it has no improved sterility mechanism and does not have other benefits related to tube thoracostomy.

Other examples include U.S. Publication No. 2009/0318898 to Dein that describes a chest tube capable of deflation to provide easier removal from the body and U.S. Pat. No. 8,128,648 to Hassidov et al. that describes a gun with an expandable cutting trocar for use in placing a chest tube. However, neither provides an improved port for transcutaneous access into the body or an improved method for maintaining sterility during placement.

Finally, U.S. Publication No. 2011/0152874 to Lyons describes a balloon dilatational chest tube apparatus and method that is an improvement over the traditional Seldinger technique, in that it partially reduces the number of steps needed. A balloon distal to a chest tube inflates and then deflates so that the chest tube can be advanced into the dilated space (and over the deflated balloon). While an improvement, this work still is limited in that the chest tube must be pushed through chest wall tissue over the deflated balloon; there is no reusable port for easier changing of clogged or misplaced chest tube(s), and it does not significantly improve the sterility of the tube thoracostomy procedure.

The prior art contains several works relevant to infection reduction and the improvement of sterility during the establishment of a percutaneous access pathway. There are several examples of flexible sheaths to maintain sterility around percutaneous catheters. For example, U.S. Pat. No. 5,807,341 to Heim; U.S. Pat. No. 6,605,063 to Bousquet; U.S. Pat. No. 5,662,616 to Bousquet; and U.S. Pat. No. 4,392,853 to Muto and U.S. Publication No. 2012/0191044 to Koike describe such sheaths around venous catheters. Similarly, U.S. Pat. No. 5,242,398 to Knoll et al.; U.S. Pat. No. 7,789,873 B2 to Kubalak et al.; and U.S. Pat. No. 3,894,540 to Bonner, Jr. describe such sheaths around urinary catheters. U.S. Pat. No. 4,767,409 to Brooks and U.S. Pat. No. 5,215,522 to Page et al. describe such sheaths around central venous pressure catheter and endotracheal tube suction devices, respectively. However, such flexible sheaths have not been described previously for chest tubes and are not optimally designed to maintain sterility in connection with a port.

U.S. Pat. Nos. 5,336,193 and 5,429,608 to Rom et al. and U.S. Publication No. 2008/0125750 to Gaissert describe bags to minimize the provider's exposure to bodily fluids during chest tube removal. However, they do not introduce reusable percutaneous access pathway ports or reduce the chance of infection to the patient during placement.

Another example is U.S. Pat. No. 7,244,245 to Purow that describes a rigid sheath device to maintain chest tube adhesion to the chest wall and prevent pneumothorax. However, this follows standard chest tube insertion techniques and provides minimal reduction of infection.

Finally, U.S. Pat. Nos. 6,905,484 and 7,135,010 to Buckman et al. describe a military chest tube over a trocar in a sterile package. However, although the sterile packaging provides some benefit in minimizing infection risk, the works do not describe a mechanism for maintaining sterility within the system after puncturing the packaging with the chest tube, as the tube then becomes exposed to the outer environment. Additionally, there is no easily reusable percutaneous access pathway established.

Regardless of use, the transcutaneous access devices and methods of the art have not before provided for accessing and/or re-accessing a body to optimally minimize iatrogenic injury, while maintaining sterility within a closed system. As such, there is a need for a device and method to do so.

Each of the patents and published patent applications mentioned above are hereby incorporated by reference.

SUMMARY OF THE INVENTION

The present invention overcomes and substantially alleviates the deficiencies in the prior art by providing improved devices and methods for forming and/or maintaining a percutaneous access pathway.

In one embodiment, the device is used to form and/or maintain a percutaneous access pathway into the pleural cavity (i.e. tube thoracostomy). This channel can then be used to introduce part of an attachment device (e.g. chest tube(s) of different sizes, pigtail catheter, endoscope, video-assisted thoracoscopic surgery device, and/or other surgical instruments), if so desired.

Under various embodiments, the initial percutaneous access pathway is formed via different methods and devices, which include the aforementioned techniques noted as background of the present invention that have been incorporated by reference. These include but are not limited to an open surgical approach; a trocar with or without an overlying catheter; a hollow needle with or without an overlying catheter; the standard Seldinger technique; a modified Seldinger technique (e.g. as described in U.S. Publication No. 2011/0152874 to Lyons); an expandable catheter; a Veress-type needle; a twisting screw or drill bit or needle; combinations of these methods and/or devices; and other methods and devices well known in the art.

In some embodiments, the initial percutaneous access pathway is formed similarly to the device and/or method described in U.S. Publication No. 2014/0046303, previously incorporated by reference herein. In one of these embodiments, such a device has an internal hollow probe and/or indicator to allow for immediate release of tension if present as described in that application. In other embodiments, the device is modified to have a non-hollow probe and/or no tension indicator.

In some embodiments, the percutaneous access pathway is established via the use of a probe and needle mechanism that automatically stops the advance of the device upon insertion into a body cavity or space (e.g. pleural space), such as also described in U.S. Publication No. 2014/0046303. This minimizes user error and allows for the device to be used on differently sized patients (e.g. with different sized chest walls). In some embodiments, one device fits all patients. In others, part (e.g. changeable access pathways of various sizes on a reusable or standard insertion device) or all of the device is differently sized for different subgroups so that the appropriately sized device can be chosen for different subgroups based on, for example, weight, age, gender, length, pre-determined size categories (e.g. Broselow scale), and/or other indicators. These differently sized components may come together in a kit, with means for determining proper sizing. Under different embodiments, the insertion device is disposable or non-disposable and different catheters and/or ports may fit onto one insertion device or have their own sized insertion devices.

Under various embodiments, the percutaneous access pathway itself is made of different materials and methods. Under some embodiments, the percutaneous access pathway is a space (potential or maintained) through body tissue; is a deformable or non-deformable catheter; is expandable and/or deflateable plastic or metal (e.g. stent, mesh, rolled material, reinforced wires); and/or is an expandable and/or deflateable catheter filled with gas (e.g. air) or fluid (e.g. normal saline). Additionally, under some embodiments the catheter is covered partially or fully with additional material(s), flexible in some cases, that can provide additional benefits when in contact with the body tissue. Examples include means to increase and/or decrease the cross-sectional area of the catheter; to reduce friction and/or the chances of tissue being pinched in the underlying catheter or mechanism; to decrease the chances of infection (e.g. antimicrobial properties); and to have drug-releasing properties (e.g. anesthetic or other anti-pain medications).

There are several embodiments with different mechanisms for expansion and/or contraction of the percutaneous access pathway, for those embodiments that contain such a mechanism. Under some embodiments, this is accomplished via expansion of the channel itself (e.g. catheter(s) filled with gas or fluid). Under one such embodiment, an inflatable catheter is strengthened sufficiently to allow it to be inserted in a deflated or partially deflated form, and then expanded to push away surrounding tissue (e.g. chest wall) sufficiently to form an internal channel (e.g. large enough accept a chest tube). Under other embodiments, the expansion and/or deflation mechanism is fully or partially separate from the expandable and/or deflate-able catheter. This mechanism can be any that changes the diameter of the area of the device inserted into the body. Under various embodiments, this mechanism is a balloon (e.g. filled with gas and/or liquid); levers or wires or rods that move to change their cross sectional area; mesh that collapses lengthwise to increase its diameter; screw or other rotational device(s) that change diameter of an overlying portion by varying its length; a collapsed catheter that expands after use of a releasing mechanism; or other mechanisms well known in the art for changing the diameter around an inserted structure. Such mechanisms can lie fully or partially underneath, around, or adjacent to the catheter, so that the catheter forms a channel in at least one stage. In different embodiments, such mechanisms for expansion and/or deflation of the channel are powered by suction, compressed gas (e.g. air, oxygen), electrical (e.g. outlet, battery), other potential energy (e.g. coiled spring, elastic band), and/or by hand (e.g. twisting a cap, pulling a trigger, compressing a syringe).

In many embodiments, the access pathway is made of a catheter and access pathway port. In some embodiments, the access pathway port allows entrance to the catheter to be reversibly or irreversibly sealed, thus preventing air and/or infection from entering the body cavity. In some embodiments, the connection of an attachment device to the access pathway port causes the access pathway port to open, thus allowing part or all of the attachment device (e.g. chest tube, surgical equipment, endoscopy camera, video-assisted thoracoscopic surgery device) to enter the body through the catheter, but not allowing air or infectious material to enter when an attachment device is not attached. In some embodiments the access pathway port and/or catheter has one or more check valves, which allow air to release from the body but not to enter the body. Under some embodiments, the access pathway port connection uses a quick connect type mechanism, to expedite attachment and simplify the procedure.

In many embodiments, the access pathway anchors, stabilizes, and/or secures the percutaneous access pathway to the body. Examples include stabilization through sutures, staples, glue, and/or tape; tension from an expanded catheter within the body wall; adhesive that holds the catheter, port, and/or larger disk onto the skin; and/or expansion of one or more balloon(s) within the body cavity, within the percutaneous access pathway, and/or externally. In various embodiments, the catheter and/or port is anchored so as to make the percutaneous access pathway perpendicular to the skin, at an angle (e.g. to facilitate internal chest tube placement or surgical access), and/or adjustable so as to allow movement to a desired angle.

Many of the embodiments of the present invention contain attachment device(s) for entrance into the percutaneous access pathway. In some of these embodiments, the attachment device includes a port that connects to the body, catheter, and/or access pathway port, so as to allow part or all of the attachment device to enter the body. In some embodiments, after attachment the attachment device has a port which can be reversibly or irreversibly opened, thus allowing part or all of the attachment device (e.g. chest tube, surgical equipment, endoscopy camera, video-assisted thoracoscopic surgery device) to enter the body, but not allowing air or infectious material to contaminate the sterile portion of the attachment device when not attached. In some embodiments, the opening of the attachment device port is caused manually by the operator (e.g. a button, lever, or switch) and in others is caused automatically by the attachment of the catheter and/or access pathway port to the attachment device and/or attachment device port.

In many embodiments, the attachment device contains an external sheath, so as to protect part or all of the internal components from the external (e.g. non-sterile) environment and to maintain sterility within. In some of these embodiments, the sheath is formed of flexible tubing (e.g. plastic), collapsible or foldable material, and/or bag or bag-like material. In some of these embodiments, the attachment device (e.g. chest tube, surgical equipment, endoscopy camera, video-assisted thoracoscopic surgery device) can be inserted, manipulated, and/or removed by the operator while the external sheath maintains sterility within at least that portion of the device that will enter the body. The attachment device can additionally be hooked up to any external hook-ups that are standard for that device type. For example, under one embodiment, the attachment device is a chest tube covered by a sheath with a distal device port. The proximal device end connects to standard chest tube drainage or suction system(s), well known in the art.

In one embodiment, the attachment device is contained fully or partially within a sheath, which connects to the percutaneous access pathway in a manner so as to maintain sterility within the sheath and thus around the attachment device even in a non-sterile operating environment. The attachment device can be transported so that the external portion of it may be contaminated, while maintaining sterility within. When about to connect to the percutaneous access pathway, the distal attachment device port is opened (or in another embodiment a distal attachment device cap is removed), thus allowing, after connection, the sterile portion of the attachment device within to extend into the body. The attachment device may be manipulated by a non-sterile operator via the external protective sheath.

In some embodiments, the invention is inexpensively manufactured with all or part of it designed to be disposed of after one use. The needle can be made of metal, such as stainless steel. Other parts may be made of metal or plastic or other suitable material. Under various embodiments, different parts are composed of a radio-opaque material and/or contain radio-opaque markers.

In another embodiment, the inventive device and method includes a means for transiently measuring and/or viewing negative pressure.

In another embodiment, the inventive device includes a means for protecting the user from a needle stick injury when removing the insertion device from the patient. Under this embodiment, such means can be arranged from any one of the many self-blunting needle mechanisms for intravenous catheters, phlebotomy, and/or Veress needles that are well known in the art. In one embodiment, this mechanism involves the automatic locking of the probe in its distally extended "blunt" configuration when the insertion device is removed from the percutaneous access pathway.

There have been illustrated and described herein methods and devices for forming and/or maintaining a percutaneous access pathway. While particular embodiments of the invention have been described, it is not intended that the invention be limited thereto, as it is intended that the invention be as broad in scope as the art will allow and that the specification be read likewise.

From the foregoing, it can be seen that the present invention provides an effective means for forming and/or maintaining a percutaneous access pathway within animals, especially humans. This percutaneous access pathway can be in the chest, abdomen, retroperitoneal, cranium, trachea, abscess, or other potential or real body cavities. Although the example of the chest with a thoracostomy procedure placing a chest tube has at times been used to illustrate the invention, this could also similarly be, for example, the abdominal cavity with a laparoscopy procedure placing an abdominal drain (which could give the benefit of repeat laparoscopy procedures without having to place new ports and/or some of these procedures being performed outside of a standard sterile operating room). This can also similarly be used with any other surgical procedures where a reusable port for repeat procedures and/or manipulation in a non-sterile environment would be of benefit.

Moreover, it should also be apparent that the device can be made in varying lengths and sizes to treat adults, children, and infants. While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, and that elements of certain embodiments can be combined with elements of other embodiments. Additional objects, advantages, and novel features of the invention will be set forth in the description which follows, and will become apparent to those skilled in the art upon examination of the following detailed description and figures. It should be understood that not all of the features described need be incorporated into a given method or device.

DETAILED DESCRIPTION OF THE INVENTION

Figure 1:
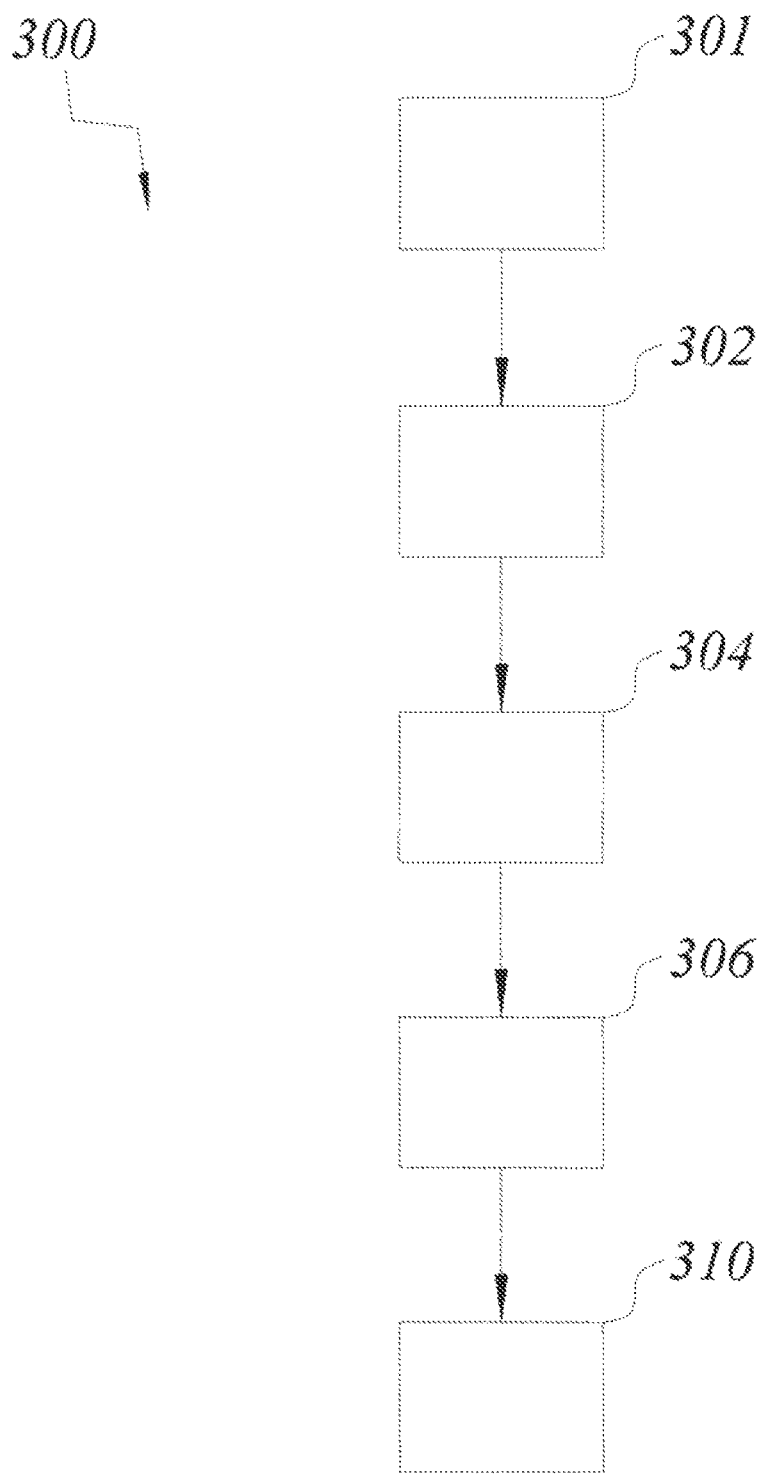
FIG. 1 is a block diagram of a method according to an embodiment of the invention for forming and/or maintaining a percutaneous access pathway.
Figure 2:
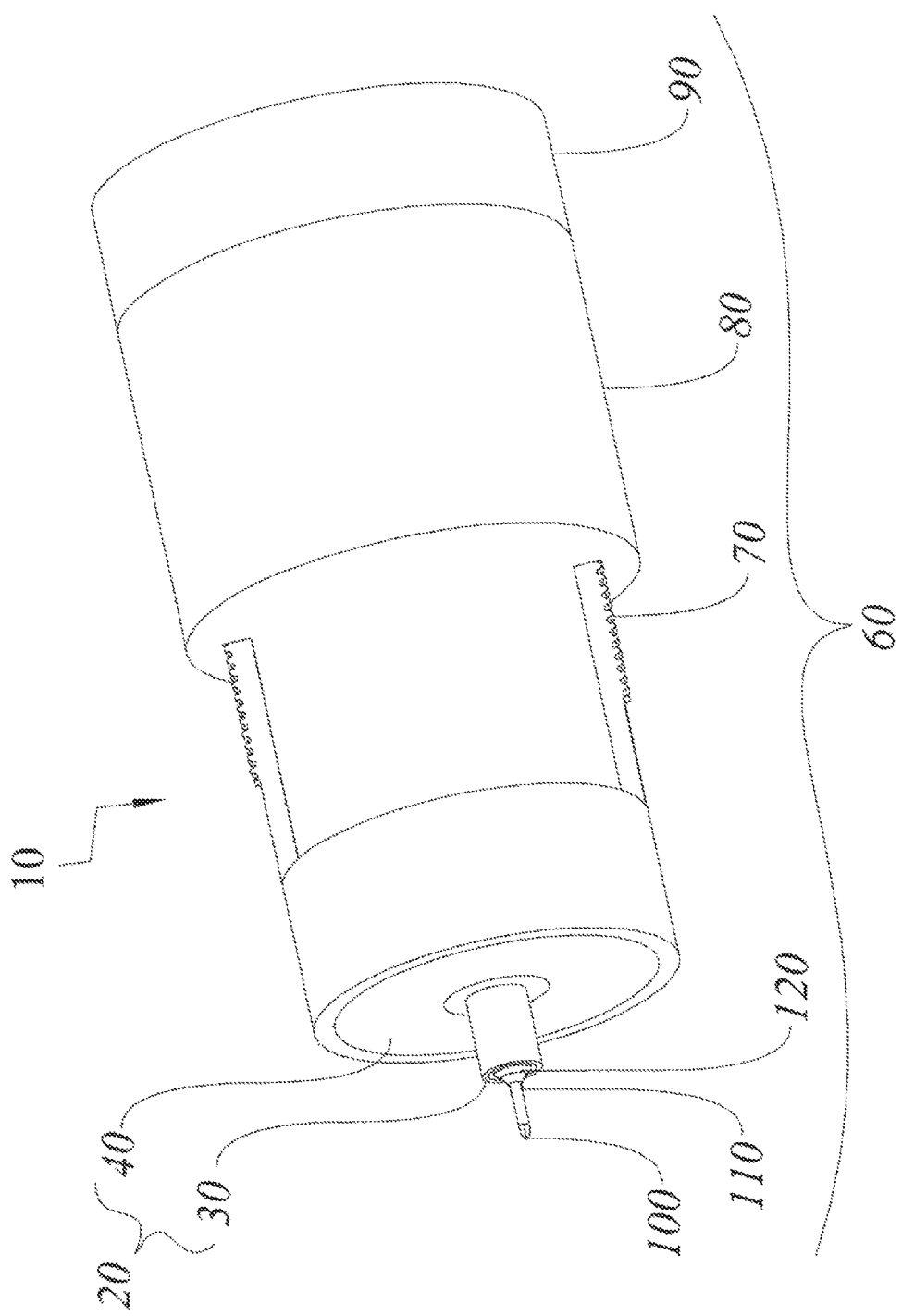
FIG. 2 is a side view of a percutaneous access pathway and insertion device in accordance with an embodiment of the invention, as assembled prior to use.

Referring to the drawings, FIG. 1 generally shows a method and workflow 300 according to an embodiment of the invention for forming and/or maintaining a percutaneous access pathway. This method and workflow 300 should be assumed to fit within standard emergency, pulmonary, and surgery protocols well known in the art (and not described here). Additionally, methods of standard needle use and safety, patient cleaning and sterilization, equipment disposal, suction setup and other standard medical practice well known in the art are not described here. The method 300 starts with providing a percutaneous access pathway at step 301. Under numerous embodiments, said access pathway includes a port and a catheter (i.e. an elongated tubular member). Under many but not all embodiments, said percutaneous access pathway also comes with an insertion device that includes a dilatational member. Under several embodiments, the dilatational member is initially positioned at least partially within the catheter and sized to dilate a portion of the body wall (e.g. chest wall) when activated.

Next, the percutaneous access pathway is inserted percutaneously into the body at step 302 (e.g. into the pleural space). Under some but not all embodiments, the device has an auto-stopping mechanism to stop the advance of the device into the body at the appropriate depth. Under several embodiments, the dilatational member then dilates to expand a portion of the body wall (e.g. chest wall). Under several embodiments, the access pathway has a port that can be reversibly connected to additional devices. Under most of these embodiments, the port remains closed by default (unless attached to another device). If a percutaneous access pathway had already been formed (e.g. during thoracic surgery, after standard incision of the chest wall or use of the Seldinger or other previously noted chest tube insertion techniques, after removal of a prior standard chest tube) then the access pathway could simply be inserted without need for an expandable catheter, insertion device, and/or dilatational mechanism. Additionally, under at least one embodiment, the percutaneous access pathway is a potential space created by the surgeon.

Next, after removal of the dilatational mechanism (in those embodiments in which it is present) the access pathway is connected by the user to an attachment device at step 304, which can then be inserted into the body. Under several embodiments, the attachment device has its own port. In some of these embodiments, the attachment device port connects to a port on the access pathway. In others, it connects directly to the skin via adhesive or other well-known means. Under numerous embodiments, the attachment device is contained fully or at least partially within a sterile sheath.

Next, the port of the percutaneous access pathway is opened at step 306, so as to provide access into the body (i.e. through the chest wall and into the pleural space). Under some embodiments, this happens concurrently with step 304 and under others happens sequentially. Under numerous embodiments, this occurs by opening a port on the access pathway and inserting the attachment device. Under several embodiments, the attachment device has a cap, which is removed before connecting it to the access pathway, and/or its own port, which opens after being connected to the access pathway port. Under several embodiments, connection of the attachment device to the access pathway allows insertion of part of the attachment device into the patient (e.g. chest tube through the access pathway and into the pleural space) via an internal sterile space, regardless of the sterility of the outer environment. Under some embodiments, this connection uses a quick connect type mechanism to expedite attachment and simplify the procedure. In various embodiments, the access pathway port opens only when attached to the attachment device. Likewise, under various embodiments, the attachment device port (if present) is opened manually via the removal of a cap and/or only when attached to the access pathway port.

Next, the attachment device is inserted into the body at step 310 (e.g. a chest tube inserted into the plural space). Under several embodiments the attachment device is contained fully or at least partially within a sterile sheath that can be manipulated by the user to insert the device into the body. Some embodiments include a means to secure the inserted portion of the attachment device at its desired depth into the body without compromising the sterility of the inserted device. Some embodiments include additional methods to secure the device to the patient, at steps 302, 304, and/or 310. Many embodiments include methods for the device to be later removed, which under some embodiments include the contraction of the access pathway.

Moving now to FIGS. 2, 3, 4, and 5, one embodiment of the present invention is illustrated and generally indicated as 10. For ease of reference, distal shall refer to the end of the device farthest away from the user, while proximal shall refer to the end of the device closest to the user.

This embodiment generally comprises an assembly 10 made up of at least one of three type of components: access pathway 20, insertion device 60, and attachment device 140. Access pathway 20 includes catheter 30 and access pathway port 40. Insertion device 60 includes access holder 70, insertion body 80, rotational cap 90, probe 100, needle 110, and expansion mechanism 120. Attachment device 140 includes device port 150, chest tube 170, sheath 180, and chest tube cap 190.

Figure 6:
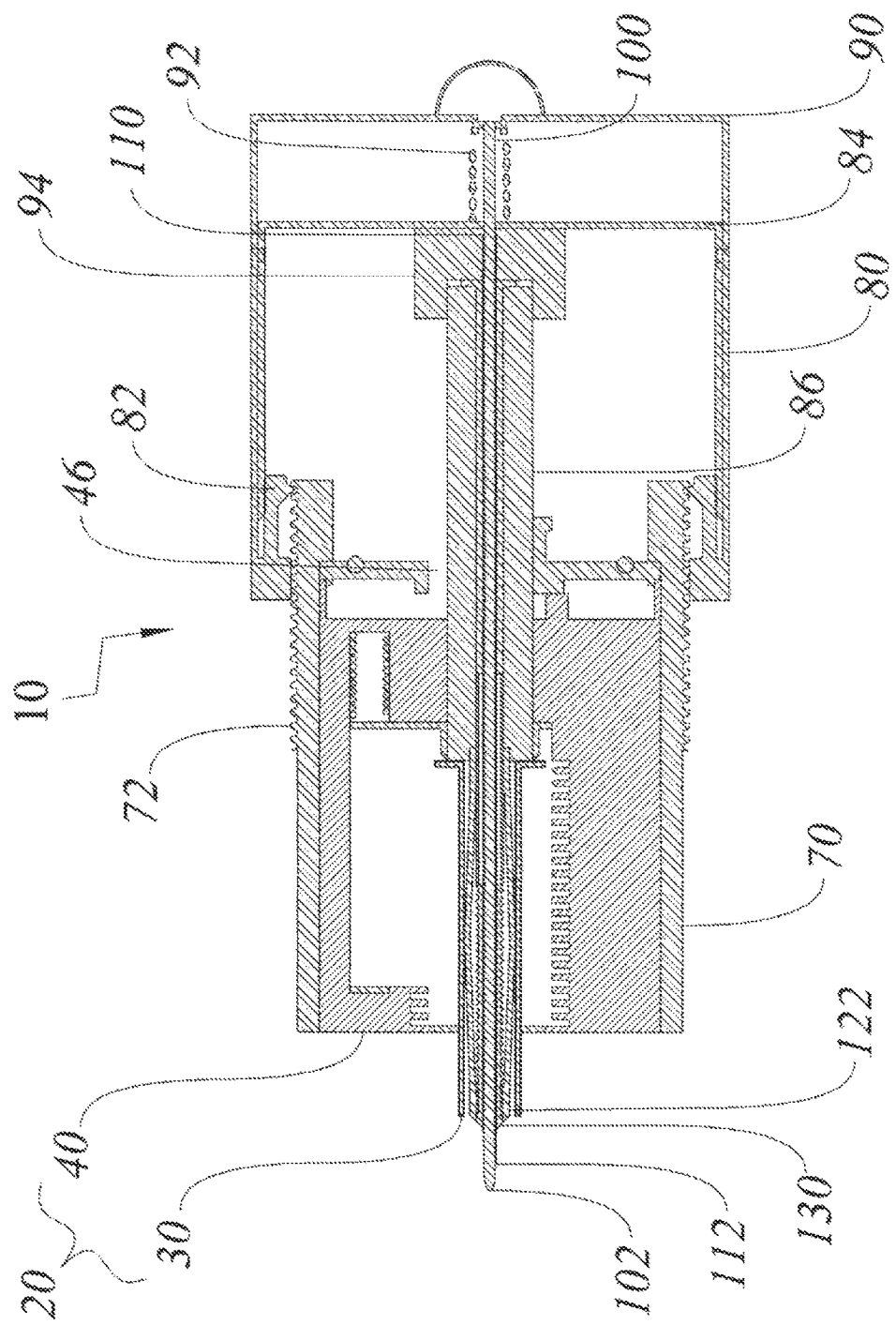
FIG. 6 is a cross-sectional side view of a percutaneous access pathway and insertion device in accordance with an embodiment of the present invention, as assembled prior to use.

Moving now additionally to FIG. 6, access pathway 20 sits within access holder 70 of insertion device 60 so that it can be removed from insertion device 60 distally but not proximally. Further, access pathway 20 includes catheter 30 sitting within access pathway port 40. Catheter 30 encloses expansion mechanism 120 in this embodiment holding tight to the opening mechanism due to the elastic nature of catheter 30. Within catheter 30 are rigid rods 32, which keep the internal passage of the catheter from narrowing at one end in comparison to the other. Access pathway port 40 contains access pathway channel 42 connecting to catheter locking area 44 and catheter release mechanism 50. As insertion prong 86 of insertion device 60 is within access pathway channel 42 and access pathway entrance 46, this causes access pathway port door 48 to remain open despite the tension placed on it to close by torsion spring 49.

Rotational cap 90 of insertion device 60 attaches onto insertion body 80 so as to allow rotational movement. Needle 110, probe 100, and expansion mechanism 120 pass into access pathway 20 and attach directly to insertion body 80. Expansion prong 122 of expansion mechanism 120 is inserted proximally onto insertion prong 86 of insertion body 80, while probe 100 is within needle 110 of hollow screw mechanism 130 of expansion mechanism 120, and all extend more proximally out the proximal portion of insertion prong 86. Rotational cap gear 91 of rotation cap 90 interlocks with dumbbell gear 96 so as to transfer rotational force from cap 90 to hollow screw mechanism 130 within locking block 94. Spring 92 biases probe holder 84, which is connected to probe 100, so that probe 100 extends distally to the end of needle 110 in its initial position. Further, in this initial position, probe holder 84 moves distally to cause prong 82 to engage with grooves 72 on access holder 70.

Figure 3:
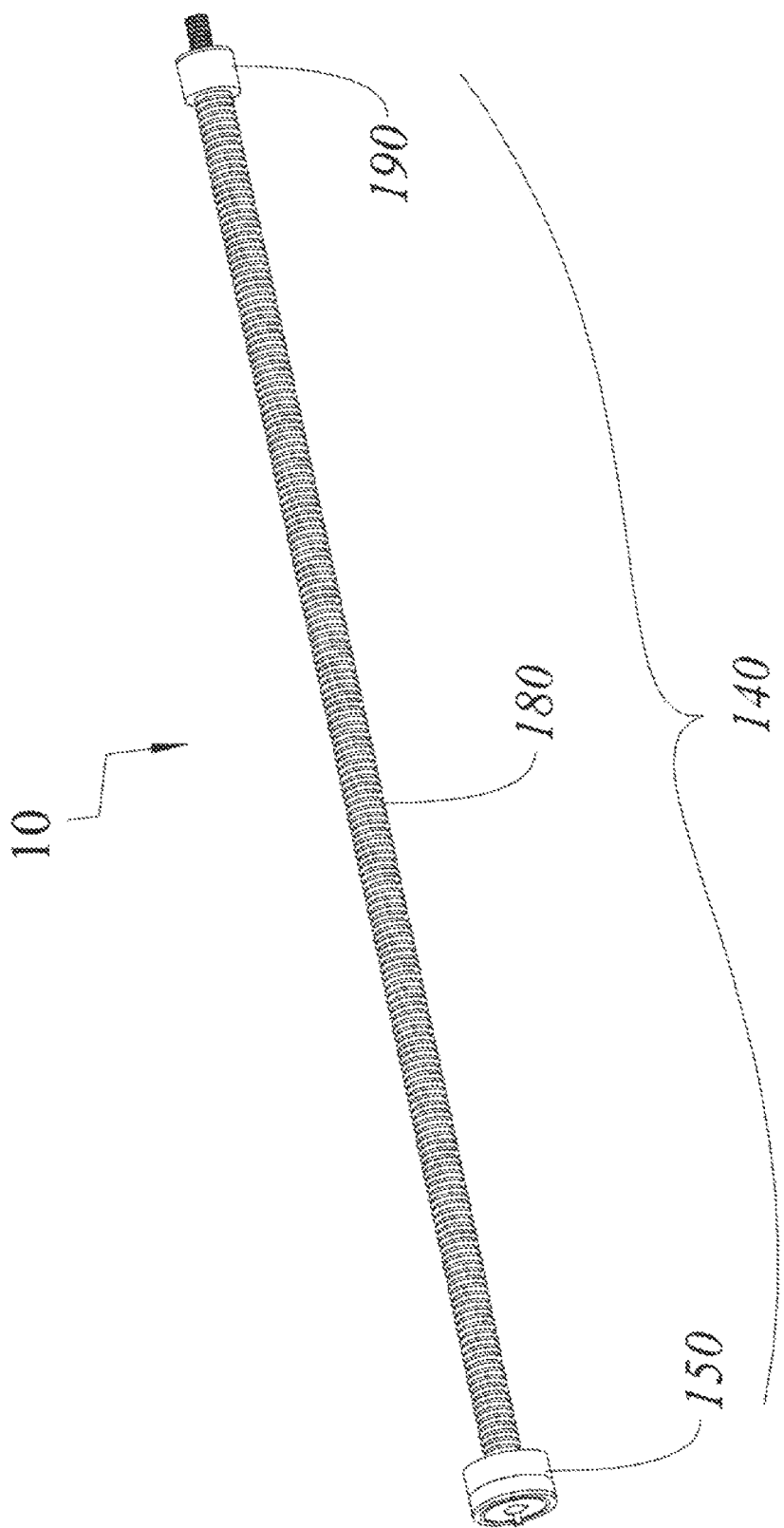
FIG. 3 is a side view of a sheathed chest tube with attaching port in accordance with an embodiment of the invention, as assembled prior to use.
Figure 4:
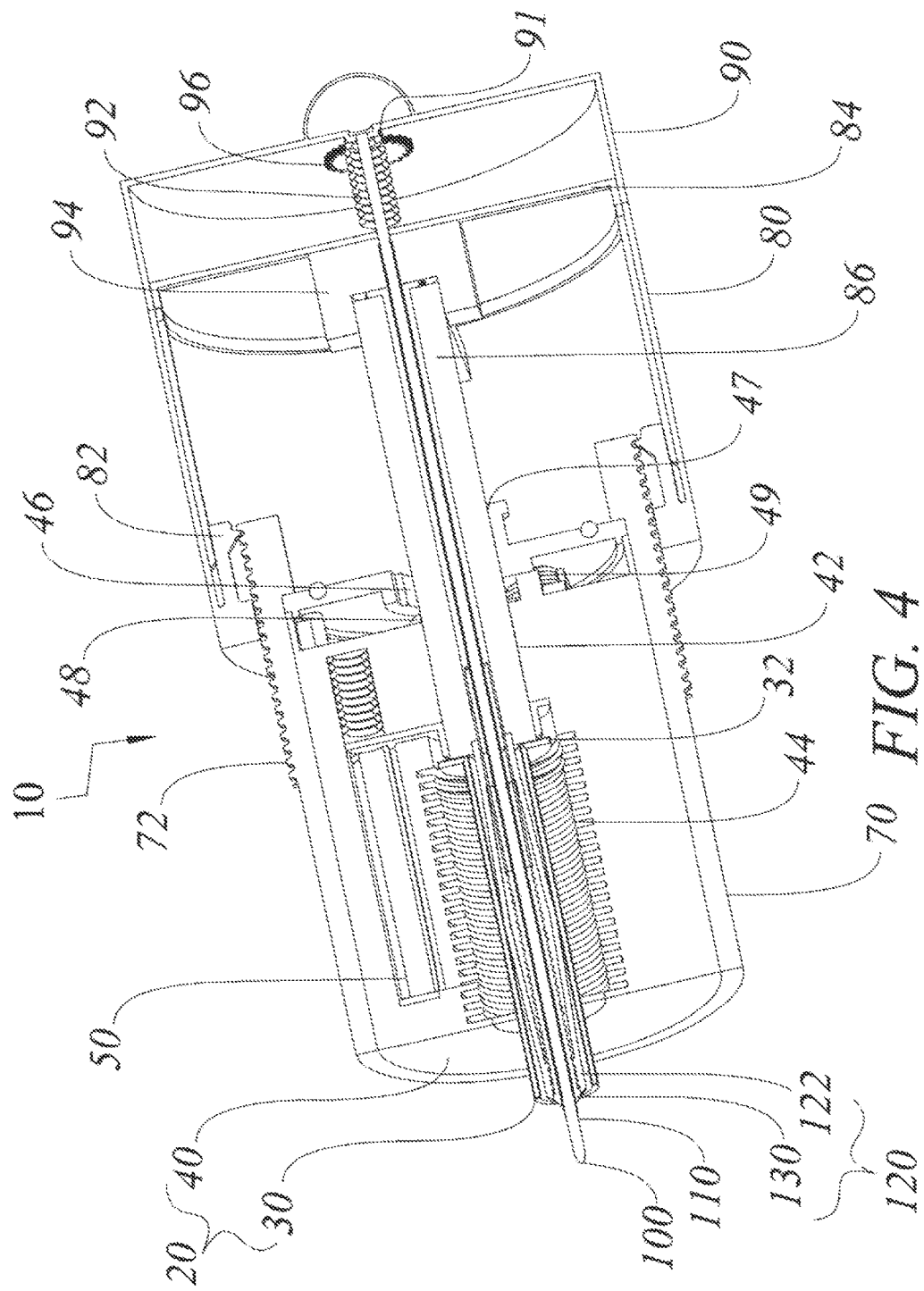
FIG. 4 is a cut-away side view of a percutaneous access pathway and insertion device in accordance with an embodiment of the invention, as assembled prior to use.
Figure 5:
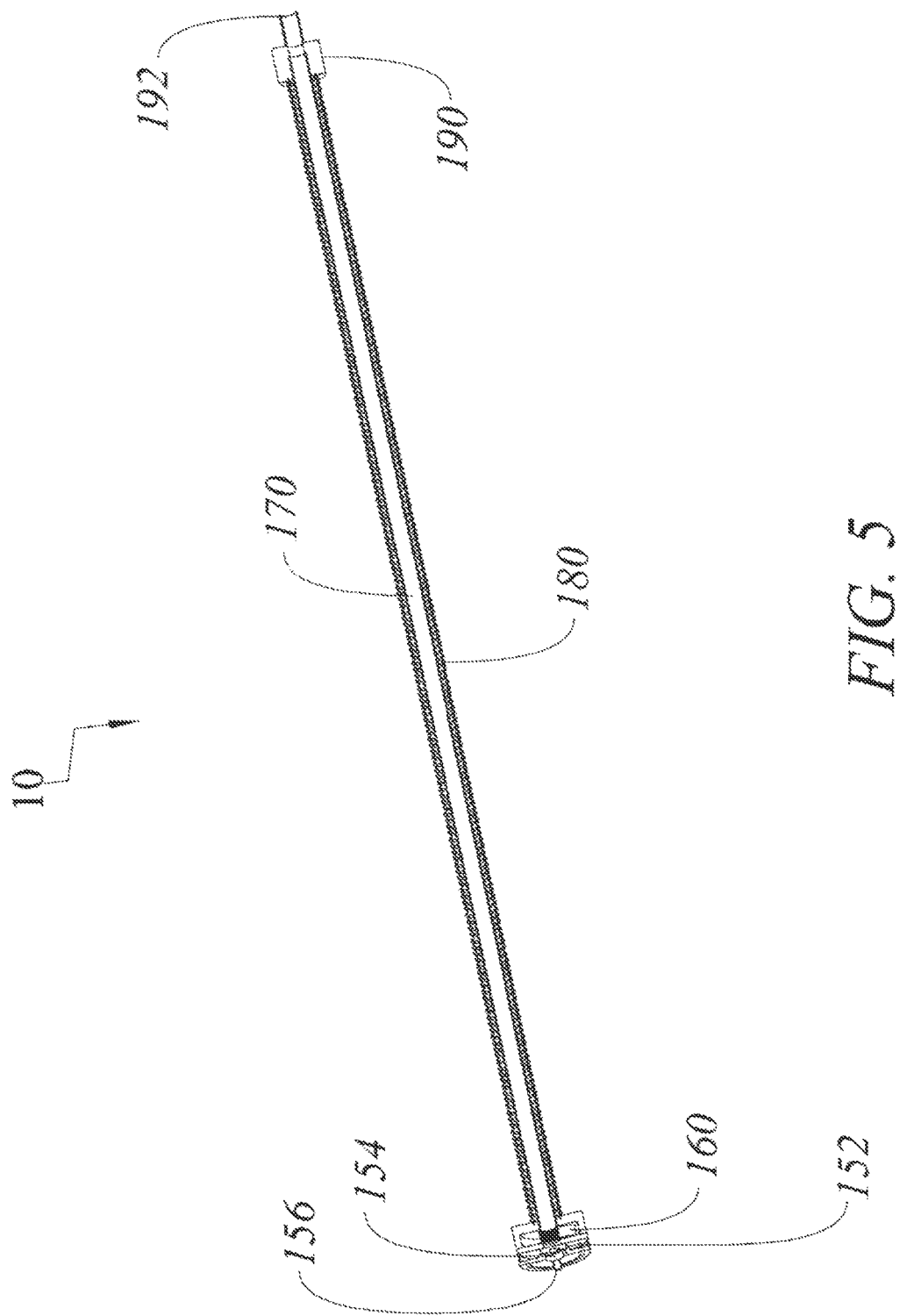
FIG. 5 is a cut-away side view of a sheathed percutaneous tube with attaching port in accordance with an embodiment of the present invention, as assembled prior to use.

Moving now specifically to FIG. 3 and FIG. 5, attachment device 140 is shown, having device port 150 at its distal end and chest tube cap 190 at its proximal end. The middle of attachment device 140 contains chest tube 170 within sheath 180. Device port 150 contains device door 152 biased to close behind device entrance 154 by a torsion spring (not shown). It also contains locking prong 156 and chest tube clamp 160. Chest tube 170 is connected to chest tube cap 190, but slides within device port 150 such that it can extend out of device entrance 154 if sheath 180 is collapsed distally by the operator. Further, the area within sheath 180 is sterile such that the chest tube within will also remain sterile despite outside manipulation due to closed door 152 and chest tube cap 190, the exit 192 of which is also in various embodiments covered with a removable cap or has an automatic door similar to device port 150. Exit 192 can be connected to suction or other standard chest tube drainage means.

Moving now additionally to FIGS. 6-14, assembly 10 of an embodiment of the invention is described in use. In FIG. 6 the assembly 10 is shown before insertion. The tip 102 of probe 100 extends out distally from the tip 112 of needle 110, due to the biasing action from spring 92 on probe holder 84 and thus probe 100 as previously described. As probe holder 84 is in its distal position, it causes prong 82 to engage with grooves 72 on access holder 70. Thus, access pathway 20 and access holder 70 are unable to move in relation to insertion body 80.

Figure 7:
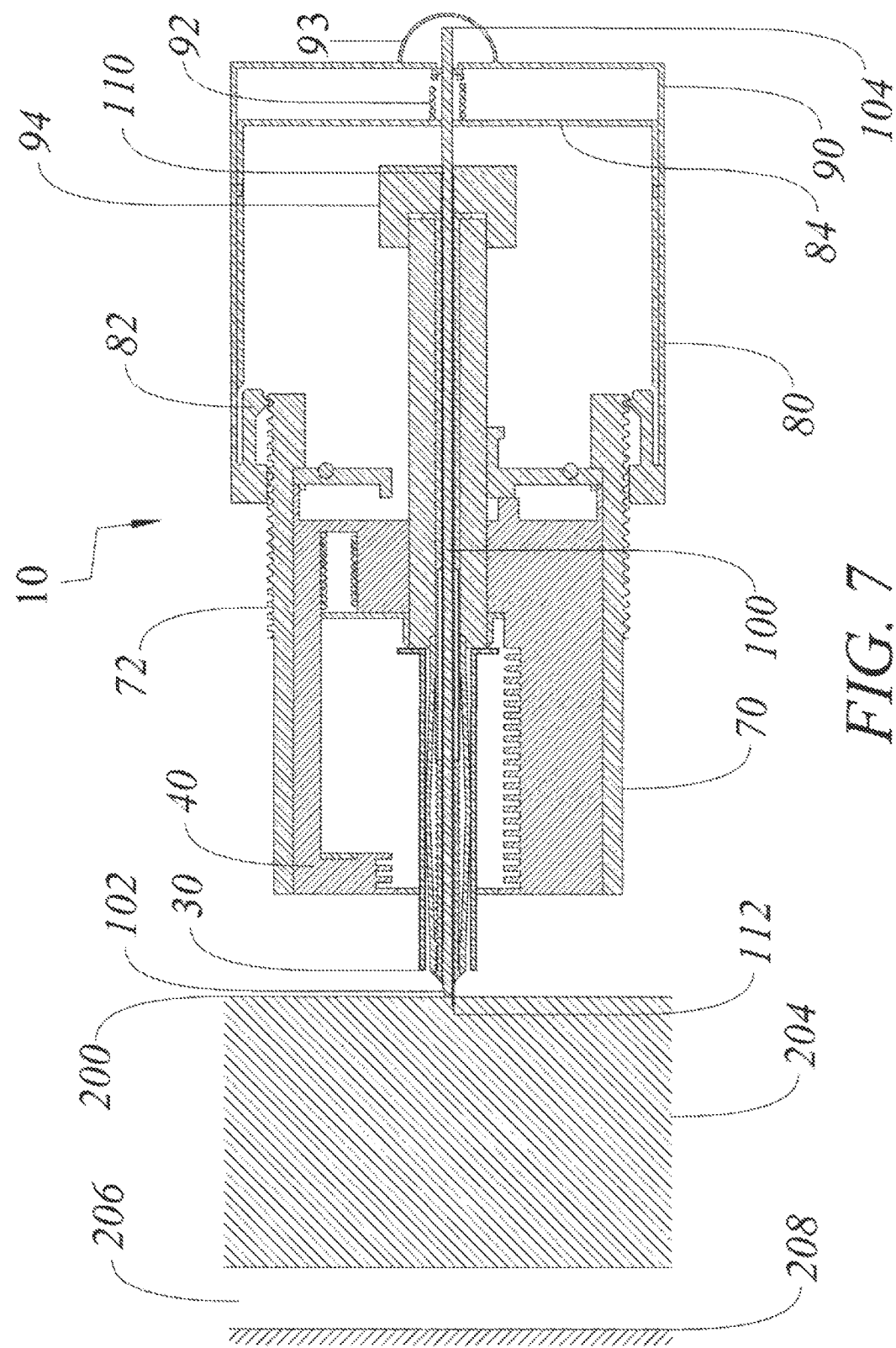
FIG. 7 is a cross-sectional side view of the device of FIG. 6, shown upon contact with the skin.

FIG. 7 demonstrates when probe end 102 first touches the skin 200 of the example of a human body, with skin 200 covering a chest wall 204 within which lies a pleural cavity 206 and lung 208. This causes probe tip 102 to move proximally in reference to needle tip 112, and likewise probe 100 to move proximally in reference to needle 110. As probe 100 is adhered to probe holder 84 and needle 110 is adhered to locking block 94 (which is further adhered to insertion body 80), this causes holder 84 to start to move proximally in relation to insertion body 80 and rotational cap 90, thus compressing spring 92. As probe holder 84 is in its proximal position, it releases prong 82 from engagement with grooves 72 on access holder 70. Thus, access pathway port 40 and catheter 30 (i.e. access pathway 20) and access holder 70 are now able to move in relation to insertion body 80. Probe tip 104 can be viewed by the operator as in its proximal position through viewer chamber 93.

Figure 8:
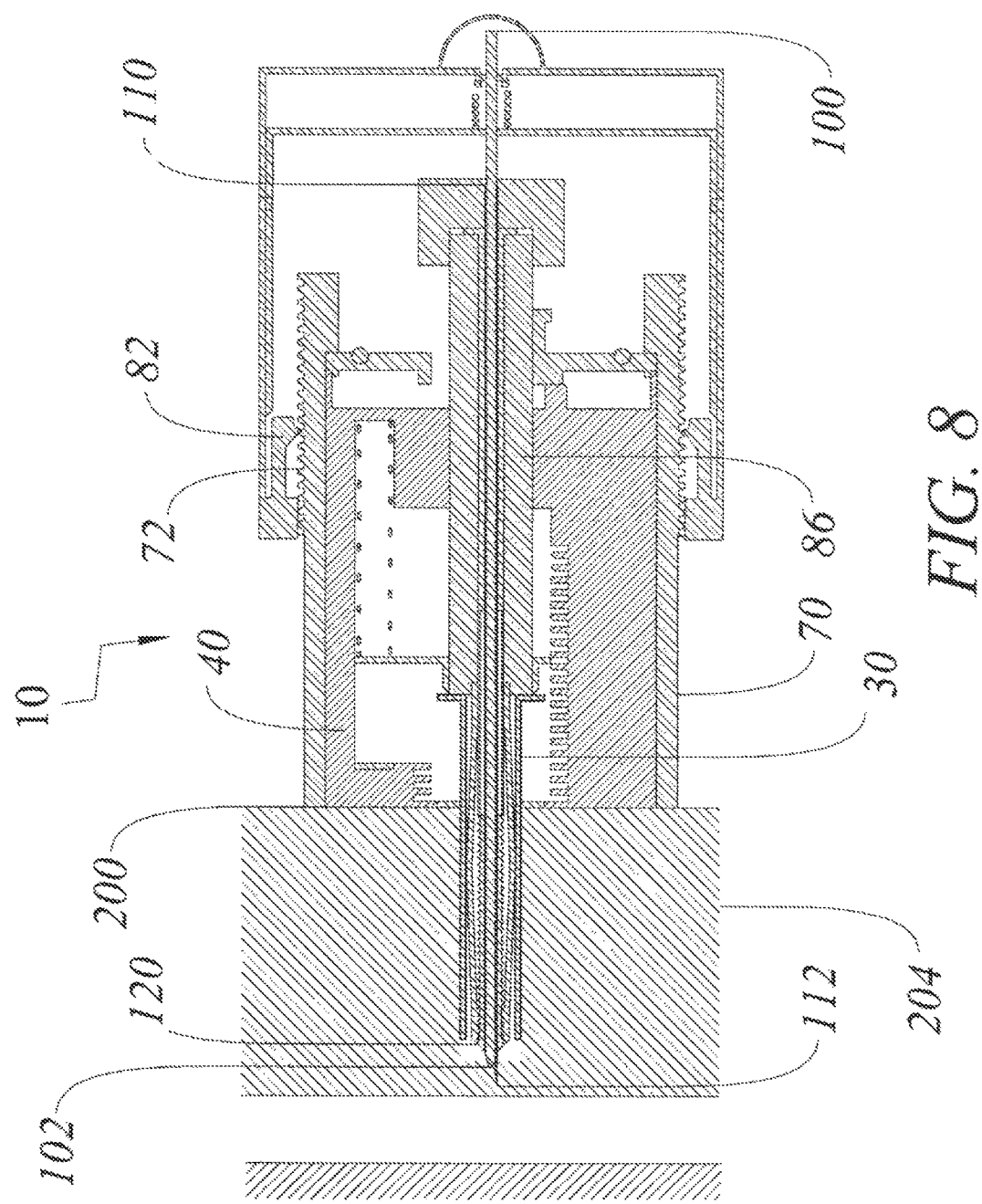
FIG. 8 is a cross-sectional side view of the device of FIG. 6, shown upon penetration of the chest wall.

Moving now to FIG. 8, when needle 110 pierces skin 200 and starts to enter chest wall 204, it causes probe tip 102 to stay proximal in reference to needle tip 112 (thus, continuing to release prong 82 from engagement with grooves 72). Once the distal portion of access holder 70 and the distal portion of access pathway port 40 touch skin 200, further distal movement of the insertion device 60 causes it to move distally in relation to access pathway port 40 and access holder 70, thus causing catheter 30 (along with probe 100, needle 110, and expansion mechanism 120) to move further into the body, pushed distally by insertion prong 86 (and insertion device 60).

Figure 9:
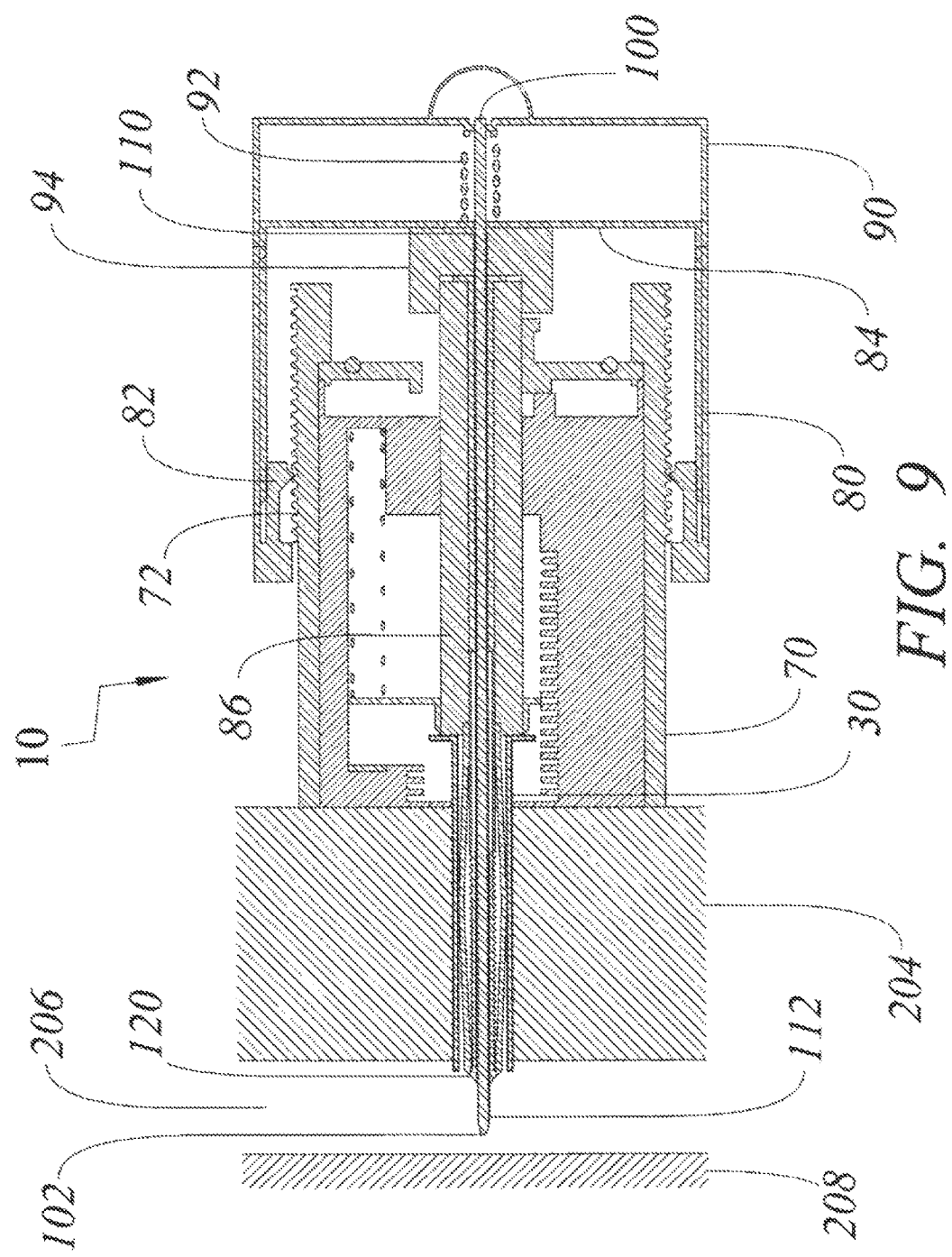
FIG. 9 is a cross-sectional side view of the device of FIG. 6, shown upon entrance into the pleural space.

Moving now to FIG. 9, once needle tip 112 pierces chest wall 204 and enters pleural space 206, spring 92 acting upon probe holder 84 forces probe 100 to move distally in relation to insertion body 80 and needle 110, thus projecting probe tip 102 distal to needle tip 112 (and serving to protect lung 208 and other vital organs from the sharp distal needle tip 112). Additionally, as probe holder 84 is in its distal position it causes prong 82 to engage with grooves 72 on access holder 70, thus inhibiting any further distal movement of insertion body 80 and stopping the distal advance into the body of insertion prong 86 and catheter 30 (along with probe 100, needle 110, and expansion mechanism 120).

Figure 10:
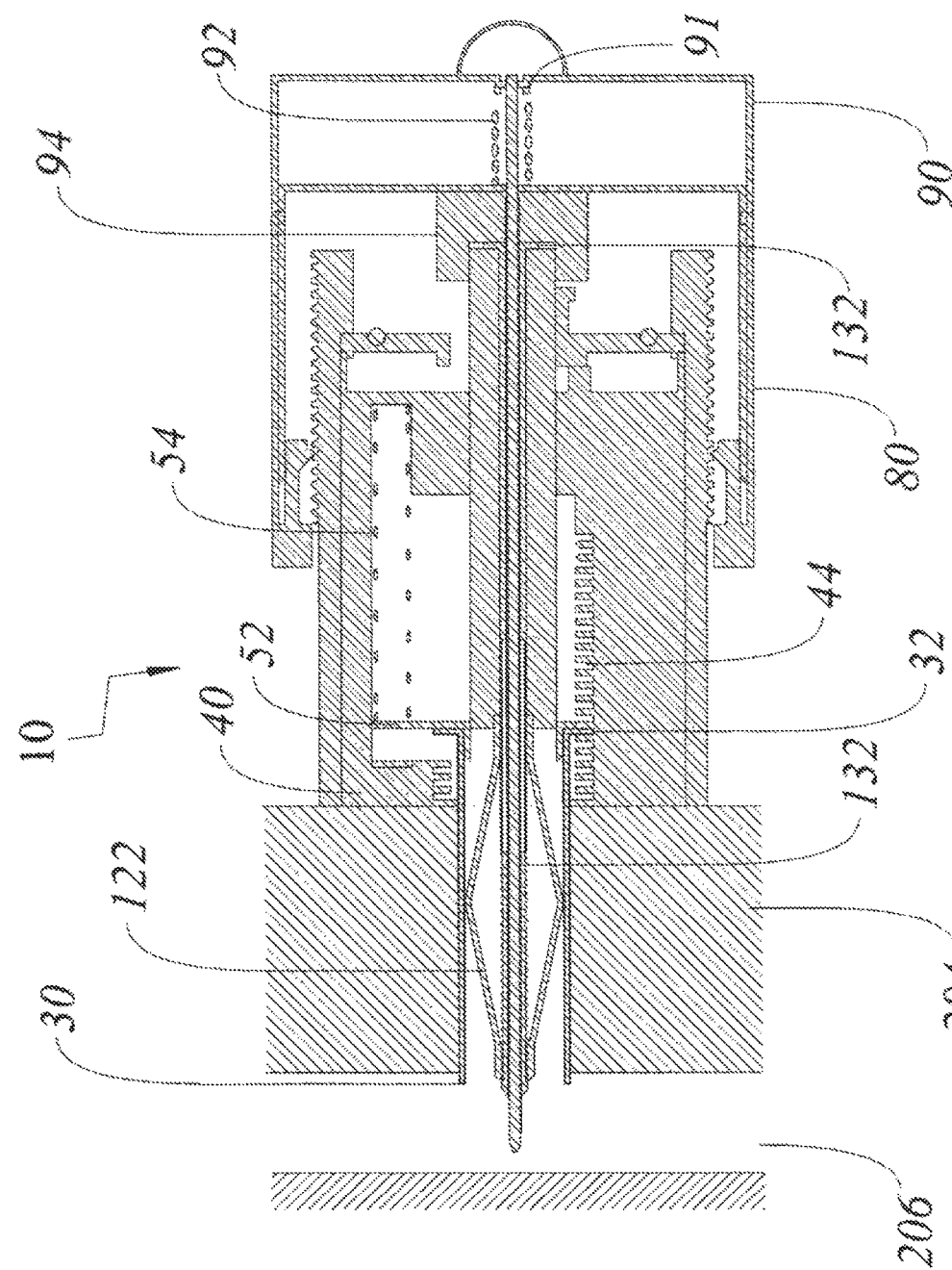
FIG. 10 is a cross-sectional side view of the device of FIG. 6, shown upon expanding transcutaneous entrance into the pleural space.

Moving now to FIG. 10, once penetrated into pleural space 206, catheter 30 is then expanded to a larger cross-sectional diameter. To do so, rotational cap 90 is rotated in relation to insertion body 80, which engages rotational cap gear 91 to cause dumbbell gear 96 (shown in FIG. 4) to rotate. Dumbbell gear 96 then transfers the rotational force to hollow screw mechanism 132 within locking block 94, which causes the distal tip of expansion prong 122 to collapse proximally, thus additionally expand it circumferentially to dilate catheter 30 and chest wall 204. Finally, once catheter 30 reaches a pre-set dilation size, catheter lock 52, which is biased distally by spring 54, moves distally inside catheter 30, thus locking catheter 30 in its expanded configuration. When so locked, catheter ridge 32 fits into catheter locking area 44 so as to inhibit proximal or distal movement of catheter 30 in relation to access pathway port 40.

Figure 11:
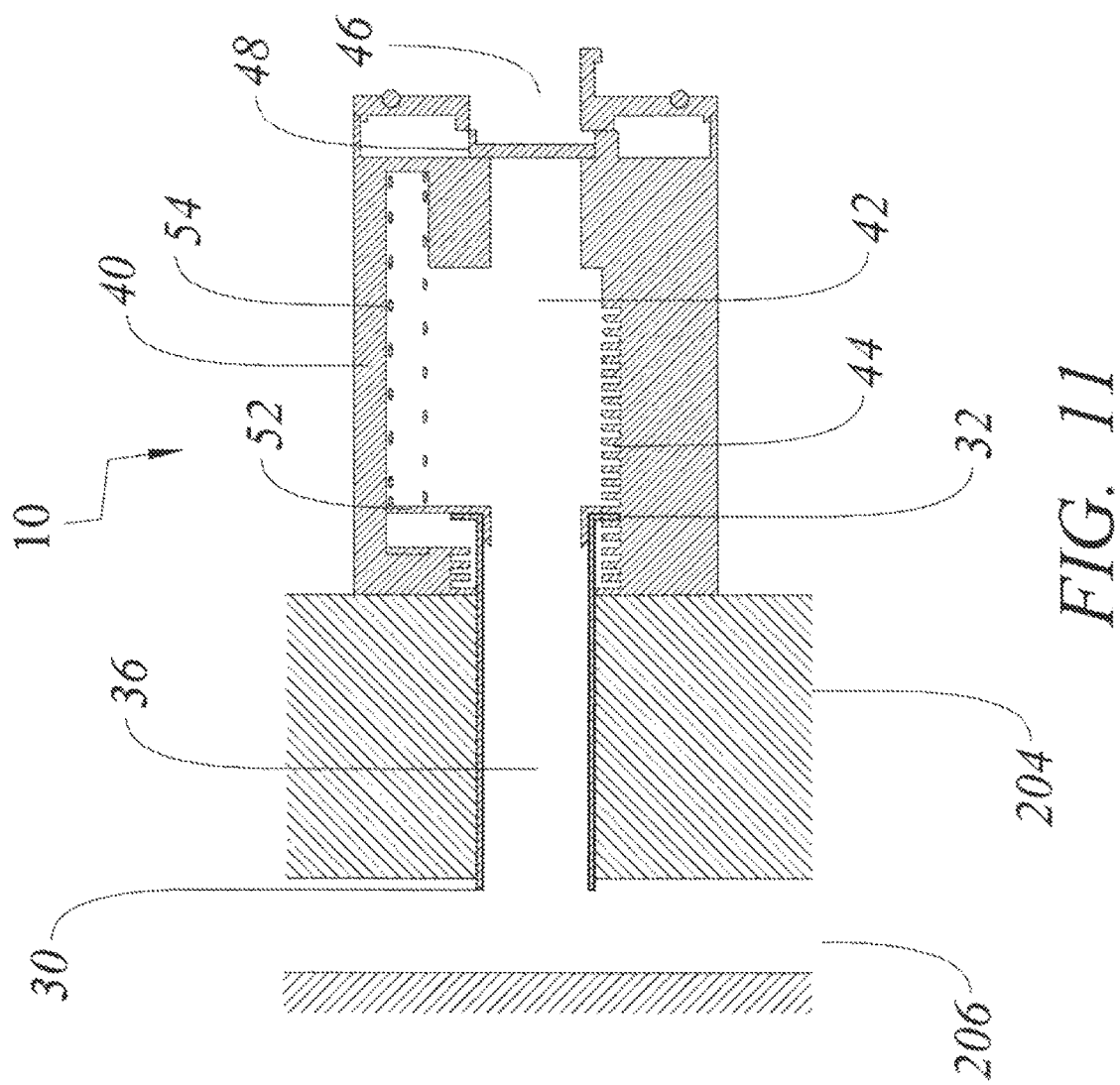
FIG. 11 is a cross-sectional side view of the device of FIG. 6, shown after removal of the insertion device.

Moving now to FIG. 11, the assembly after removal of insertion device 60 (not depicted) is shown, with access pathway port 40 and catheter 30 (i.e. access pathway 20) secured onto the body using any of the aforementioned techniques. Catheter 30 remains in its expanded configuration due to catheter lock 52 (held distally by spring 54) and cannot move proximally or distally in relation to access pathway port 40 due to catheter locking area 44 around catheter ridge 32. With the removal of insertion device 60, there is a free pathway from pleural space 206 through chest wall 204 via the inside chamber 36 of catheter 30 and the access pathway 42 of access pathway port 40. This pathway is only obstructed to the external environment by access pathway port door 48, which has automatically closed after removal of insertion prong 84 (shown in FIG. 10) due to the biasing of torsion spring 49 (shown in FIG. 4). Thus, no air or infection may enter the body through access pathway 20. At this or a prior or later stage, access pathway port 40 and catheter 30 (i.e. access pathway 20) may additionally then be secured to the patient by one of the many common means of adhering devices to patient skin known in the art (e.g. tape, glue, suture, staples, etc.).

Figure 12:
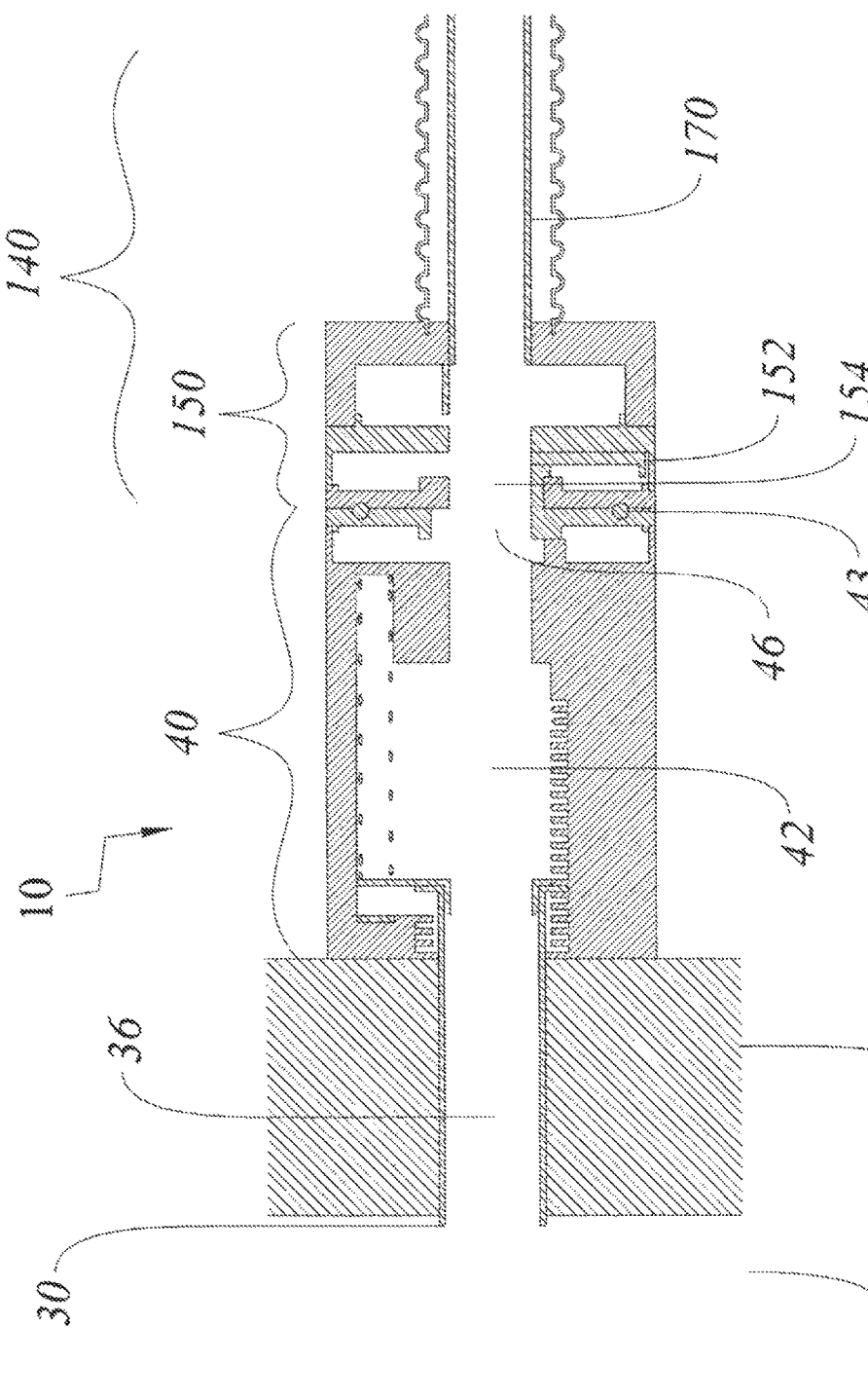
FIG. 12 is a cross-sectional side view of the devices of FIGS. 3 and 6, shown after locking on the sheathed chest tube mechanism.

Moving now to FIG. 12, the assembly upon reversible connection of attachment device 140 to port 40 is shown. Access pathway port 40 and device port 150 both have similar mechanisms that allow the two to securely connect via their respective locking keys (47 and 156, shown in FIGS. 4 and 5) and that upon rotation in relation to each other force the opposite port door to open (48, shown in FIG. 4, and 152). This mechanism only allows the port doors to open when an opposing port is attached and prohibits removal of the connected port until the doors can close fully, which provides the benefit of ensuring an internally sterile space. If placed after the exterior of access pathway port 40 has become unsterile, the proximal portion of access pathway port 40 should be cleaned with a sterilizing agent, just prior to connection to device port 150. Device port 150 can be similarly cleaned prior to use or may have an additional cap distally, which is removed just prior to use to maintain sterility beneath it and on the distal surface of device port 150. Access pathway port 40 also contains O-ring 43, which assists in ensuring an airtight seal between the two connecting ports. Once both ports are connected, there is an uninterrupted transcutaneous access pathway from pleural space 206 through the inside catheter chamber 36, and the access pathway port access pathway 42, catheter door 46, and device port door 154 to chest tube 170.

Figure 13:
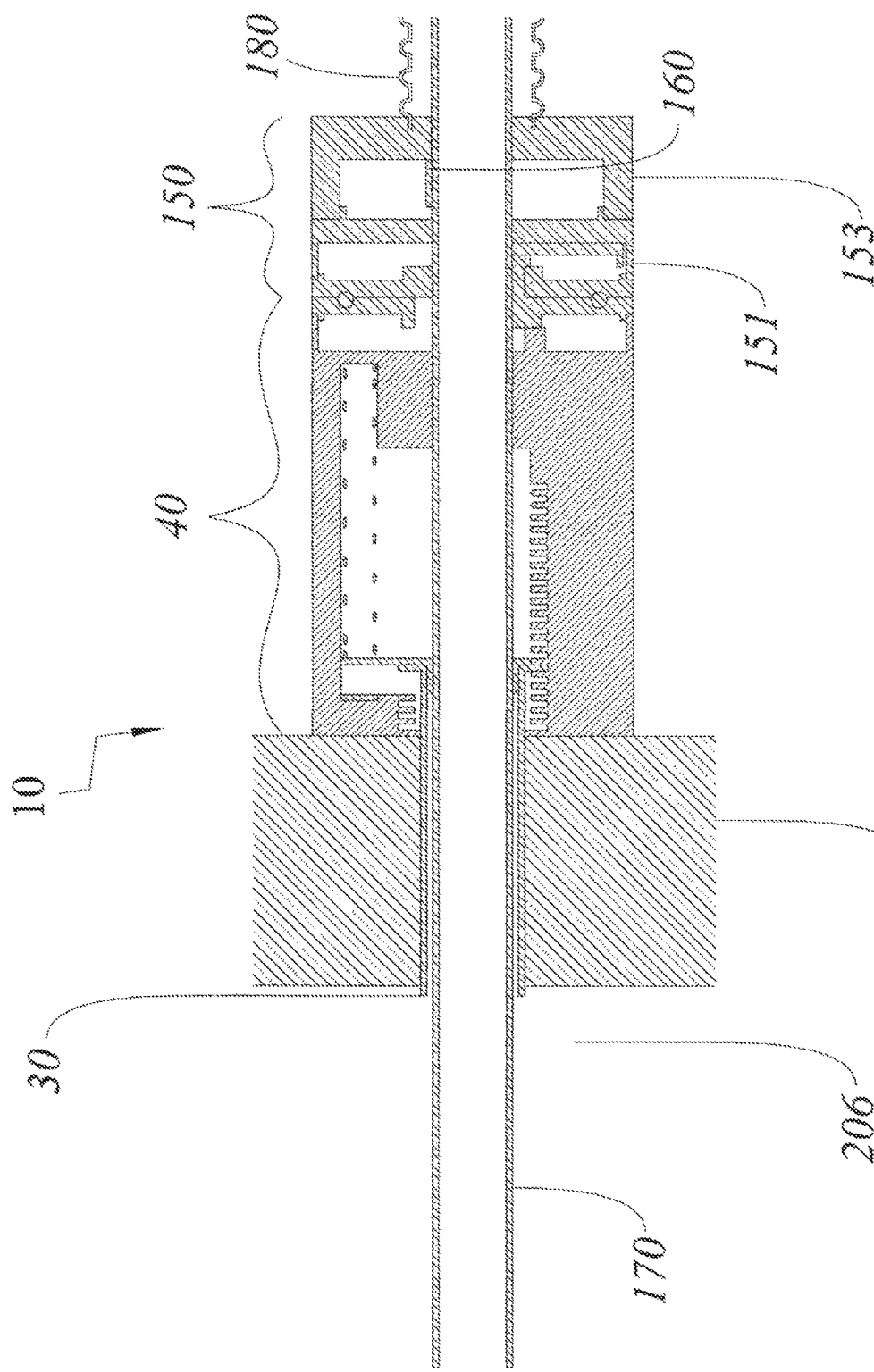
FIG. 13 is a cross-sectional side view of the devices of FIGS. 3 and 6, shown after partial insertion of the slide-able internal chest tube.

FIG. 13 shows the assembly upon insertion of chest tube 170 through access pathway port 40 and catheter 30 (i.e. access pathway 20). As there is an uninterrupted transcutaneous access pathway within port 40, catheter 30, and device port 150, chest tube 170 can be manipulated by the operator within collapsible sheath 180 to slide it distally through catheter 30 (within chest wall 204) and into pleural space 206. Clamp 160 of device port 150 can then be engaged to hold chest tube 170 at the desired length within the body. Since chest tube 170 is in place, port doors 48 and 152 (described previously) cannot close, and thus the ports remain locked onto each until removal of chest tube 170.

Figure 14:
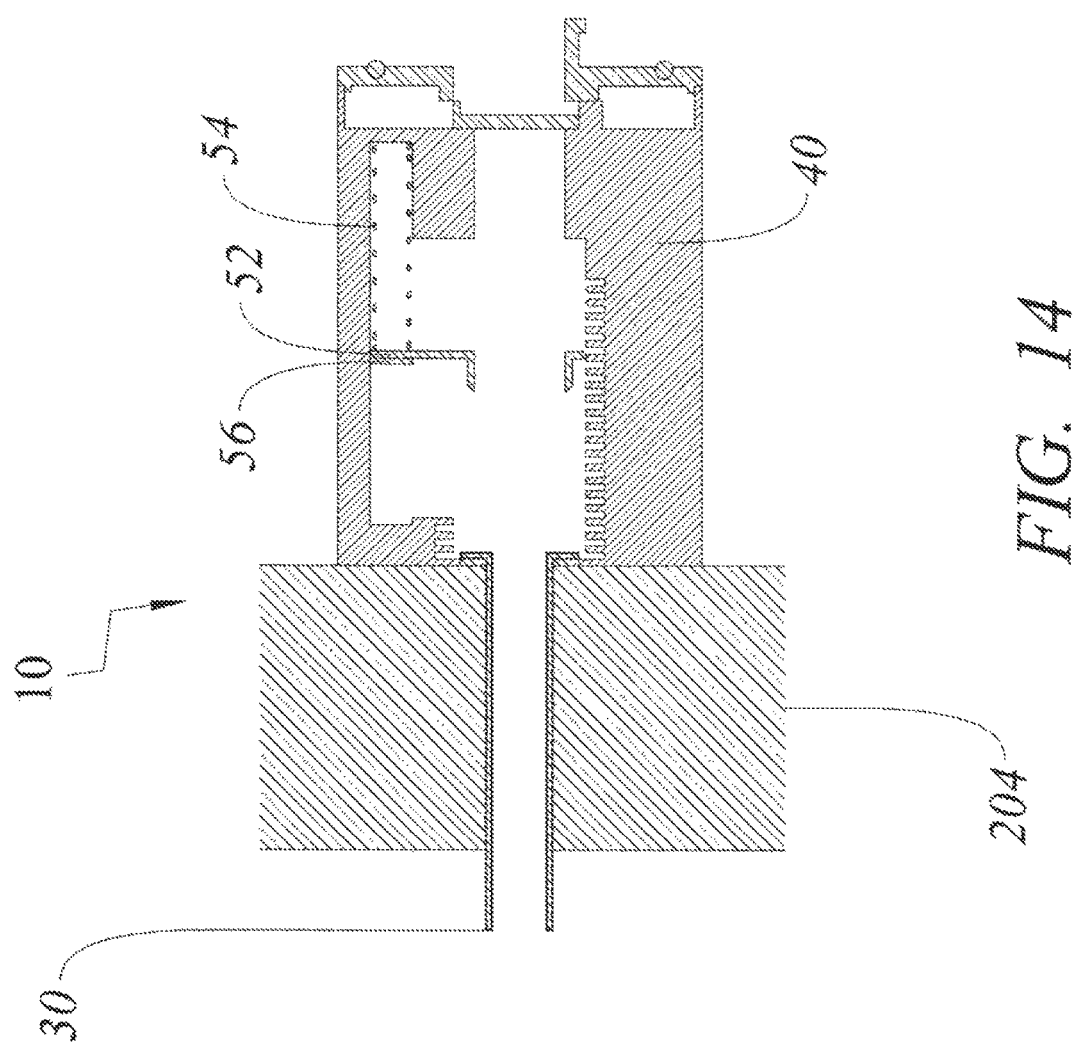
FIG. 14 is a cross-sectional side view of the devices of FIGS. 3 and 6, shown after removal of the chest tube sheath device and with the internal dilating catheter mechanism released.

FIG. 14 shows the assembly in the middle of removal, after the disengagement of attachment device 140 (no longer shown). Catheter release 56 is pulled proximally, overcoming spring 54 and thus moving catheter lock 52 proximally. This releases catheter 30 to collapse and reduce its cross-sectional diameter, thus making it easier to remove it from chest wall 204. Catheter 30 can then be pulled out proximally by pulling on access pathway port 40.

Figure 15:
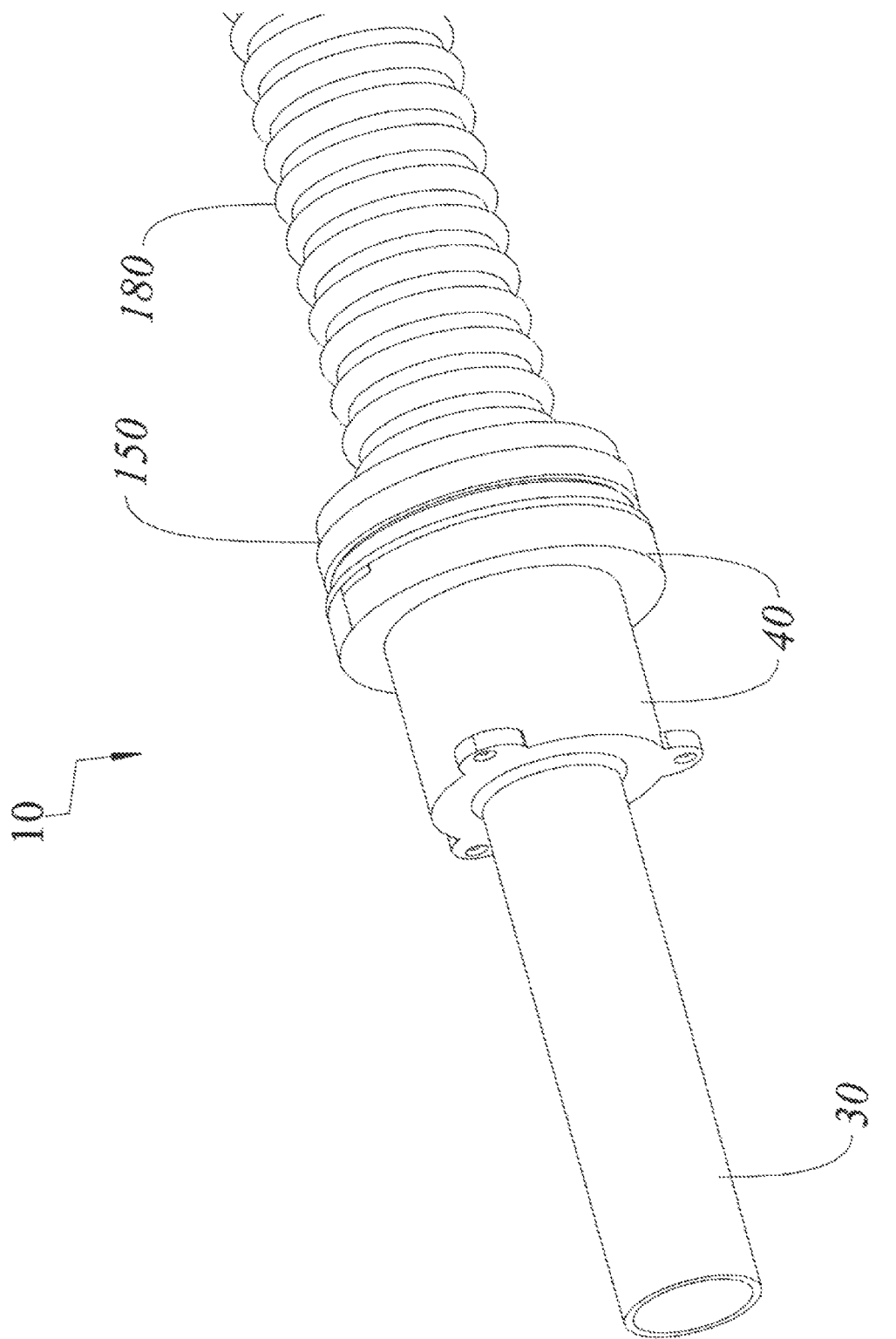
FIG. 15 is a side view of percutaneous access pathway and attachment devices in accordance with an embodiment of the invention, shown when attached to each other.
Figure 16:
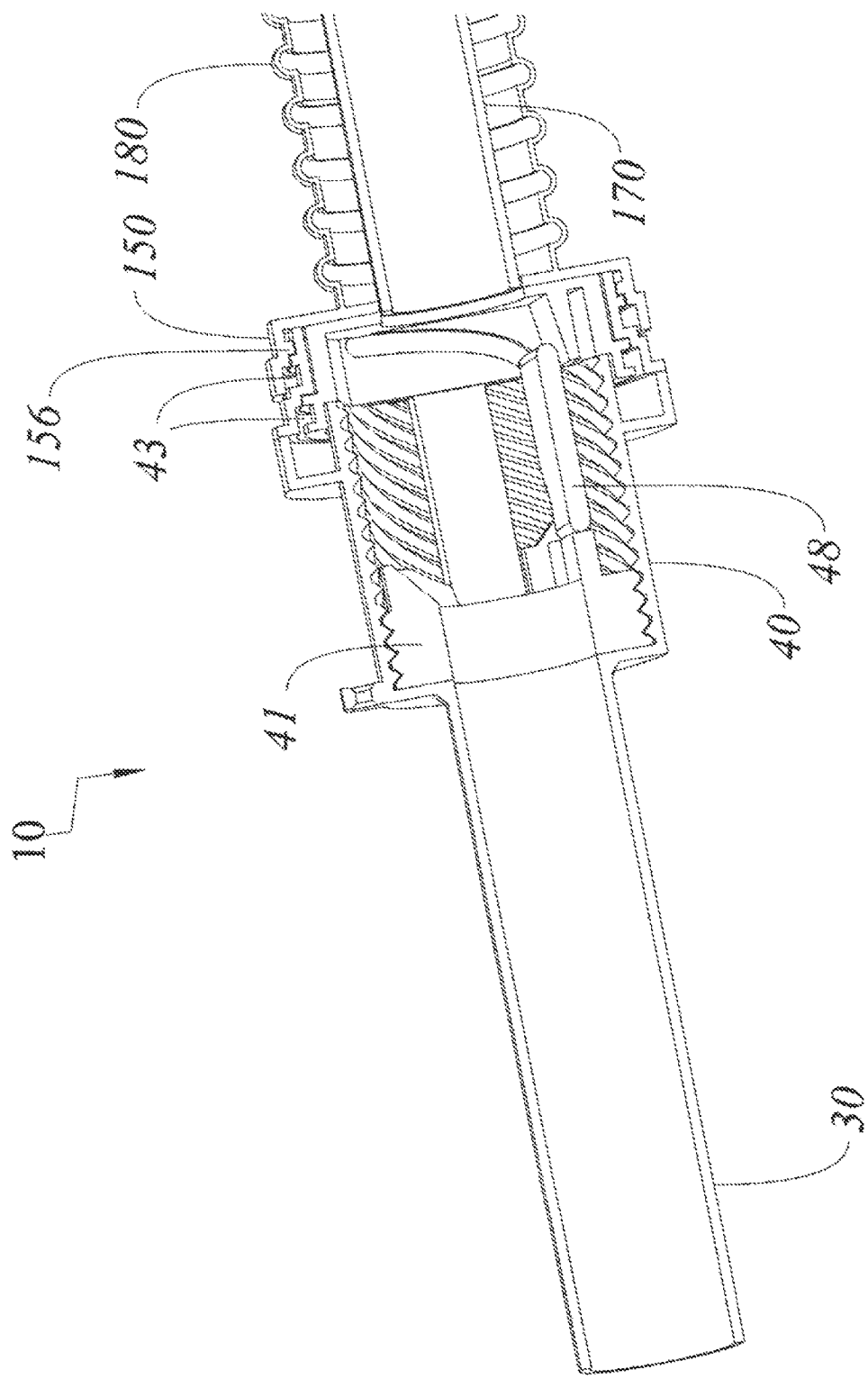
FIG. 16 is a cut-away side view of percutaneous access pathway and attachment devices in accordance with an embodiment of the invention, shown when attached to each other.

Moving now to FIGS. 15 and 16, an example of another embodiment of device 10 of the present invention device is illustrated. FIG. 15 shows access pathway 20, consisting of catheter 30 and access pathway port 40, reversibly connected to attachment device, consisting of device port 150, chest tube (not shown), and sheath 180. Access pathway 20, in this embodiment, is inserted into the body to sit flush with the skin (not shown) and does not vary the length of catheter 30 extending out of access pathway port 40 as in the previous embodiment, thus reducing parts and complexity. Device port 150 connects via a quick-lock fashion with access pathway port 40 to reversibly connect the two components.

FIG. 16 shows the internal workings of this embodiment. In this embodiment, access pathway port 40 and device port 150 attach to each other via an integrated locking mechanism 156, which upon rotation of attachment device 140 reversibly locks it to access pathway port 40 while causing the port door 48 to open. This mechanism allows port door 48 to open only when device port 150 is attached, which provides the benefit of ensuring an internally sterile space. In this embodiment, there is no door on attachment device 140, but rather a cap that keeps the distal end of device port 150 sterile until it is removed prior to use (not shown). Access pathway port 40 also contains areas for O-rings 43, to ensuring an airtight seal between the two connecting ports (and also internally within access pathway port 40).

Additionally, FIG. 16 shows that, under this embodiment, the rotation of access pathway port 40 and device port 150 in relation to each other causes a screw mechanism to move door holder 41 linearly within port 40, thus opening or closing door 48, with door 48 biased to the closed position by a spring (not shown). When chest tube 170 is inserted through port 40, door 48 is unable to close and thus attachment device 140 is unable to be removed from access pathway 20 until chest tube 170 is pulled out.

There have been illustrated and described herein methods and devices for forming and/or maintaining a percutaneous access pathway. While particular embodiments of the invention have been described, it is not intended that the invention be limited thereto, as it is intended that the invention be as broad in scope as the art will allow and that the specification be read likewise.

Furthermore, it will be appreciated by those skilled in the art that the device can be used on other types of potential spaces and body cavities. Examples include the abdominal cavity, trachea, skull and other bones, vessels, bladder and other hollow organs, as well as abscesses and other collections of fluid (e.g. empyema, ascites, and pleural and other effusions).

For example, it will be appreciated by those skilled in the art that the access pathway of the current invention may function as a standard catheter, Penrose drain, pigtail catheter, chest tube, tracheostomy tube, endotracheal tube, venous or arterial catheter, thoracentesis tube, paracentesis tube, abscess drainage or other medical tube or catheter for placement into a body cavity. Furthermore, it will be appreciated by those skilled in the art that the current invention may be used for placing access pathways into the abdominal cavity, abscess(es), the thoracic cavity, the cranium, bone, the trachea, veins, arteries, and other organs and/or potential spaces.

Furthermore, while parts of embodiments of the invention were described as having certain shapes, and being made of certain materials, it will be appreciated that other materials and shapes can be utilized. It will therefore be appreciated by those skilled in the art that yet other modifications could be made to the provided invention without deviating from its spirit and scope as so claimed.

The invention claimed is:

1. A device for forming and/or maintaining a percutaneous access pathway into a body of a patient, comprising:
   an access pathway catheter configured to connect an internal portion of a body of a patient to an external environment;
   an access pathway port configured to maintain a barrier between the internal portion of the body and the external environment when in a closed position, the access pathway port including a distal opening through which the access pathway catheter is configured to extend into the internal portion of the body;
   an attachment device connectable to the access pathway port and configured to selectively cause the access pathway port to open by opening one or more doors in the access pathway;
   an internally sterile attachment device sheath at least partially surrounding the attachment device and configured to enable insertion of at least part of the attachment device into the internal portion of the body through the one or more doors in the access pathway when the attachment device is connected to the access pathway port; and
   an insertion device configured to cause the access pathway catheter to be inserted into the internal portion of the body of the patient, wherein the insertion device is configured to selectively cause the access pathway catheter to expand.

2. The percutaneous access pathway of claim 1, wherein the one or more doors in the access pathway includes a door in the access pathway port that is configured to be reversibly opened and closed.

3. The percutaneous access pathway of claim 1, wherein the attachment device is configured to be reversibly connected to and disconnected from the access pathway port.

4. The percutaneous access pathway of claim 1, wherein the attachment device is configured to be manipulated from the external environment through the attachment device sheath while maintaining a barrier from the external environment to within the body with the access pathway port and the attachment device sheath.

5. The percutaneous access pathway of claim 1, wherein the internal portion of the patient's body is the chest cavity.

6. The percutaneous access pathway of claim 1, wherein the access pathway catheter and access pathway port are unitarily formed as a single component.

7. The percutaneous access pathway of claim 1, wherein the access pathway is configured to be used for a tube thoracostomy.

8. The percutaneous access pathway of claim 1, wherein the internal portion of the patient's body is inside the abdominal cavity, trachea, skull, bone, vessel, bladder, a hollow organ, abscess, and/or a collection of fluid in the body.

9. The percutaneous access pathway of claim 1, wherein the access pathway functions as a standard catheter, Penrose drain, pigtail catheter, chest tube, tracheostomy tube, endotracheal tube, venous or arterial catheter, thoracentesis tube, paracentesis tube, abscess drainage or other medical tube, and/or a catheter for placement into a body cavity.

10. The percutaneous access pathway of claim 1, wherein the access pathway is used for placing an access pathway into an abdominal cavity, abscess, thoracic cavity, cranium, bone, trachea, vein, and/or artery.

11. The percutaneous access pathway of claim 2, wherein the access pathway is configured to enable opening of the door in the access pathway port when the attachment device is connected to the access pathway port.

12. The percutaneous access pathway of claim 2, wherein the access pathway is configured to inhibit removal of the attachment device from the access pathway port while the door in the access pathway port is open.

13. The percutaneous access pathway of claim 1, wherein the attachment device is configured to connect to suction in the external environment.

14. The percutaneous access pathway of claim 1, wherein the attachment device sheath is air-impermeable.

15. The percutaneous access pathway of claim 1, wherein the access pathway port and/or access pathway catheter contain an adhesive configured to secure the access pathway to the body of a patient.

* * * * *